United States Patent [19]
Tisserat et al.

[11] Patent Number: 6,060,314
[45] Date of Patent: May 9, 2000

[54] UTILITY-HIGH CARBON DIOXIDE AND LIGHT QUALITY AND QUANTITY IN WOODY PLANT PROPAGATION

[75] Inventors: Brent Tisserat, Metamora; Kenneth Eskins, Laura, both of Ill.; Bryan Kaphammer, Plainsboro, N.J.; George Tull, Levittown, Pa.; Steve R. Wann, Richmond Hall, Ga.

[73] Assignee: Union Camp Corporation

[21] Appl. No.: 09/126,896

[22] Filed: Jul. 31, 1998

Related U.S. Application Data

[60] Provisional application No. 60/054,359, Jul. 31, 1997.
[51] Int. Cl.$^7$ ............... A01G 7/02; A01H 3/02; A01H 4/00; A01H 5/00; A01H 7/00
[52] U.S. Cl. ............ 435/420; 435/422; 47/58.1; 47/65.5
[58] Field of Search .................... 47/58.1, 65.5; 435/420, 422

[56] References Cited

U.S. PATENT DOCUMENTS 3,931,695  1/1976  Widmayer .................. 47/58

OTHER PUBLICATIONS

Flygh et al., Optimizing growth of conifer seelings in vitro. Ann. Sci. For. 46 suppl., Forest Tree Physiology, E. Dreyer et al., eds., 168s–170s, 1989.

Sionit et al., Woody plant reactions to CO2 Enrichment. Carbon Dioxide Enrichment of Greenhouse Crops., vol. II, Enoch et al eds, 70–85, 1986.

Axelsson et al., Oak Seedlings Grown in Different Light Qualities Part 1 Morphological Development. Physiol. Plant. 45:387–392, 1979.

Fortser et al., Influence of Blue light on the Photosynthetic Capacity of marine Plants from Different Taxonomic, Ecological and Mortpological Groups. European Journal of Phycology. vol. 29, No. 1, pp. 21–27, 1994.

*Primary Examiner*—David T. Fox
*Assistant Examiner*—Anne Marie Grünberg
*Attorney, Agent, or Firm*—Dechert Price & Rhoads

[57] ABSTRACT

The present invention relates to the propagation of plants and plant tissue. In particular, the present invention provides a method for propagating woody plant material comprising culturing the material in the presence of carbon dioxide in excess of about 1000 $\mu$l/l and pulses of filtered light. In another embodiment, the present invention relates to a propagation method comprising culturing the plant material in excess of about 7000 $\mu$l/l of carbon dioxide and further exposing the plant material to pulses of filtered light.

14 Claims, 16 Drawing Sheets

UTILITY-HIGH CARBON DIOXIDE AND LIGHT QUALITY AND QUANTITY IN WOODY PLANT PROPAGATION This claims the benefit of copending provisional U.S. application Ser. No. 60/054,359, filed Jul. 31, 1997.

FIELD OF THE INVENTION

The present invention relates to the propagation of woody plants, plant cells and tissue cultures. In particular, the present invention provides a method for such propagation.

Increasing the rate of photosynthesis in a plant, resulting in increased growth of plant material, is a goal having a significant economic outcome once realized. Economic benefits include increased rate of propagation, as well as improved efficiency of propagation by enhancing survival and early growth. These benefits are especially important for plants propagated from tissue culture. The culture conditions having an impact on growth and photosynthesis that are controllable include temperature, wavelength and intensity of light and period of exposure thereto, growth medium, and atmospheric gas concentrations.

Varying the concentration of carbon dioxide has been explored. See Flygh et al., *Ann.Sci.For.*, 46 suppl., 168s–170s (1989); Wittwer, in *Carbon Dioxide Enrichment of Greenhouse Crops, Volume I. Status and $CO_2$ Sources* (H. Z. Enoch and B. A. Kimball, Eds., 1986; hereinafter) (hereinafter, "*Enoch and Kimball*"), pp. 3–15; Sionit and Kramer, in *Enoch and Kimball*, pp. 70–85. For example, $CO_2$ enrichment in vitro has been associated with growth responses such as increases in dry weight (Kozai et al., Symposium Florizel on Plant Micropropagation in Hort. Ind., pp. 135–141 (1987); Cournac et al., Plant Physiol., 97, 112–117 (1991); Fujiwara, et al., *J.Agr.Met.*, 48 49–56 (1992)), plant height (Cournac et al., supra; Figueira et al., *J.Amer.Soc.Hort.Sci.*, 116, 585–589 (1991)), fresh weight (Buddendorf-Joosten and Woltering, *Sci.Hort.* 65, 11–23 (1996)), or leaf area (Buddendorf-Joosten and Woltering, supra; Figueira et al., supra).

In woody plants it has been noted that increased $CO_2$ concentrations increase the dry weight of, for example, conifer seedlings exposed to carbon dioxide concentrations of up to about 3500 $\mu l/l$ (about ten times the ambient concentration of $CO_2$ which is about 350 $\mu l/l$ of $CO_2$); beyond that point, no further benefit in dry weight increase has been noted relative to control plants. Flygh et al., supra. Other studies using woody plants have shown that $CO_2$ concentrations at triple ambient levels or higher produced no greater increase in growth than a concentration of about double ambient, and in some experiments growth at 900 $\mu l/l$ or more was less than at 675 $\mu l/l$ of $CO_2$. Sionit and Kramer, supra at 71. Prior studies conducted in greenhouses suggest that 1000 $\mu l/l$ $CO_2$ is optimum for most plants. Enoch and Kimball, *Carbon Dioxide Enrichment of Greenhouse Crops*, Vol. 1 (CRC Press Inc., Boca Raton, Fla., 1986). The use of $CO_2$ at greater than the 1000 $\mu l/l$ level is considered unnecessary and is often detrimental to the growth of plants. Id.

Varying the wavelength of light provided to plants and the duration of the plants exposure thereto has also been explored. For example, photomorphogenesis is a well-documented phenomenon that is affected by the wavelength of light to which the developing plant is exposed. See, for example, Eskins et al., *J. Plant Physiol.*, 147, 709–713 (1996); Seibert et al., *Plant Physiol.*, 56, 130–139 (1975). However, the effect of combining the wavelength and enhanced carbon dioxide levels used to accelerate growth of woody plants is not an area that has been explored previously. Nor has combining either or both of these factors to enhance tissue culture propagation.

The present invention is directed to the use of ultrahigh $CO_2$ levels and light quality and quantity in plant propagation. Propagation may either be by conventional means (seedlings or cuttings) or by plant tissue culture (micropropagation or somatic embryogenesis). These and other aspects of the inventions are set forth herein below.

SUMMARY OF THE INVENTION

The invention relates to a method for propagating woody plant material comprising exposing the plant material to a pulse of filtered light. The culturing can occur in vitro such as in tissue culture, or in non-aseptic conditions, such as in soil or soilless medium. The woody plant material can be tissue culture, seedlings, cuttings, somatic or zygotic embryos, or microshoots from tissue culture. Preferably, the material is from sweetgum, sycamore, oak, green ash, Douglas fir, Populus spp., Eucalyptus spp., Pinus spp., Acacia spp., Picea spp., Larix spp., Abies spp., or Gmelina trees. In one embodiment, the pulse of filtered light is substantially only red light. In another embodiment, the method further comprises the step of culturing the plant material in excess of a concentration of carbon dioxide of 1,000 $\mu l/l$. Preferably, the concentration of carbon dioxide is greater than about 1,000 $\mu l/l$ to about 50,000 $\mu l/l$. Still more preferably, the concentration ranges from about 7,500 $\mu l/l$ to about 30,000 $\mu l/l$. In still another embodiment, the method further comprises the steps of introducing the plant material into a chamber, and introducing and removing a nutrient medium into and from the chamber.

The invention further relates to culturing woody plant material in excess of a concentration of carbon dioxide of 7,000 $\mu l/l$, preferably from about 7,000 $\mu l/l$ to about 50,000 $\mu l/l$. In one embodiment, the method further comprises the step of exposing the plant material to a pulse of filtered light. In one embodiment, the filtered light comprises substantially red light. In another embodiment, the method further comprises the steps of introducing the plant material into a chamber, and introducing and removing the nutrient medium into and from the chamber. Preferably, the pH value of the medium is monitored and adjusted to maintain a pH value of between about 4 and about 6. Still more preferably, the plant material is exposed to about sixteen continuous hours of unfiltered light out of every twenty-four hours.

BRIEF DESCRIPTION OF THE DRAWINGS

The foregoing summary, as well as the following detailed description of preferred embodiments of the invention, will be better understood when read in conjunction with the appended drawings. It should be understood, however, that the invention is not limited to the precise arrangements and instrumentalities shown. In the drawings.

DETAILED DESCRIPTION OF THE INVENTION

Figure 1:
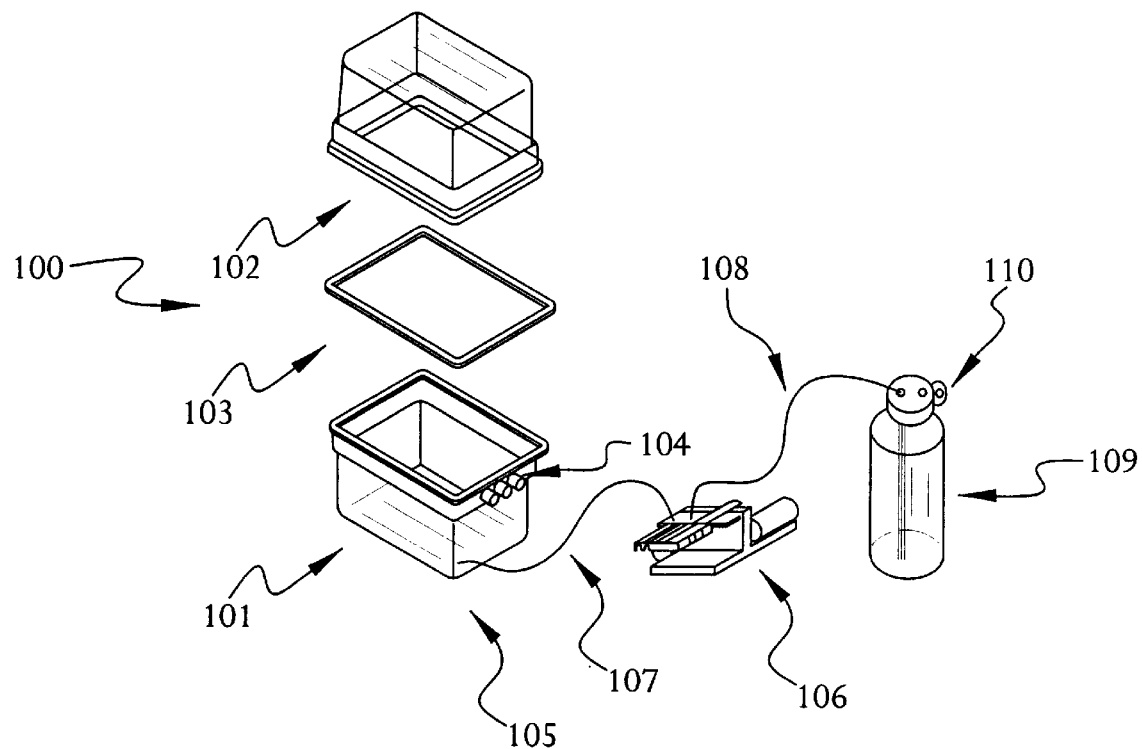
FIG. 1 is a diagram of one embodiment of a bioreactor for propagation of plant material.

The present invention relates to the propagation of plant material under conditions of carbon dioxide concentration that preferably exceeds 1000 $\mu$l/l, more preferably is from about 3500 $\mu$l/l to about 50,000 $\mu$l/l, yet more preferably is from about 7000 $\mu$l/l to about 30,000 $\mu$l/l, and even more preferably is from about 7500 $\mu$l/l to about 30,000 $\mu$l/l. One embodiment of the present invention includes use of a carbon dioxide concentration of from about 10,000 $\mu$l/l to about 25,000 $\mu$l/l. The carbon dioxide used in this invention can be provided from cylinders of carbon dioxide from commercial providers, such as Air Products Incorporated, mixed with ambient atmosphere as appropriate on site, or from cylinders of ambient atmosphere adjusted to the appropriate concentrations of carbon dioxide. The levels of carbon dioxide in the chamber of a bioreactor can be measured using a carbon dioxide sensor, such as a $CO_2$ electrode (Diamond General, Ann Arbor, Mich.).

Varying the carbon dioxide concentration under which the plant material is grown is accommodated by use of a chamber in which the plant material is grown and protected from other species that could outcompete the plant material of the plants of interest. Such a chamber can be constructed from any suitable material, such material being impassable or substantially impassable to microbes or aqueous solutions, but permitting passage of light energy without substantial filtering thereof except with respect to use of filtered light, such as to provide substantially red light, as further discussed below. Accordingly, a preferred material for construction of the chamber is any untinted transparent autoclavable material, such as, but not limited to, standard untinted clear polycarbonate (e.g., Biosafe™ Containers from Nalgene) or glass (e.g., Pyrex®). An alternative embodiment provides a chamber having transparent tinted polycarbonate or glass, such as, for example, a red-tinted such chamber. The chamber is preferably contacted with one or more suitable ports for accepting or venting gas, such as, for example, ambient atmosphere or ambient atmosphere supplemented with varying concentrations of carbon dioxide, such as supplementation in increments of 2500 $\mu$l/l from about 1000 $\mu$l/l to at least about 50,000 $\mu$l/l.

The chamber is also constructed with one or more suitable ports for accepting or removing culture medium, which can be pumped into or removed from the chamber by means of mechanical pumps, such as a peristaltic pump, or by means of hydrostatic pressure. The volume of the chamber is preferably at least about twice the volume of the culture medium employed when introduced and resident in the chamber ("the resident medium volume"), wherein the additional volume not occupied by the plant material is predominantly situated above the plant, thereby providing "head room" for growth and maximal gas exchange of the plant material. More preferably, the chamber volume is at least about 4–5 times that of the resident medium volume; yet more preferably at least about 10 times; and even more preferably at least about 50 times. The resident medium volume, as herein defined, is at least the amount of culture medium required to submerge the inert substrate on which the plant material is supported in the chamber of the bioreactor, such that at least the bottom side of the plant material is in contact with the culture medium. Irrespective of this definition which is provided for determination of the volume of the chamber, in some embodiments, a greater proportion of the plant tissue is in contact with the culture medium, such that, for example, the plant material can be partially or entirely submerged in the culture medium.

An embodiment of the bioreactor of the present invention is diagrammed in FIG. 1. As shown in FIG. 1, the bioreactor growth chamber 100 consists of a transparent base 101 and a transparent cover 102, between which is a silicone gasket 103. The chamber 100 includes ports 104 used as air vents for exchange of gases. Toward the bottom of the transparent base of the bioreactor is another port 105 that is attached to a peristaltic pump 106 by silicon tubing 107, which in turn is attached to a medium reservoir 109 having at least one air vent 110, which attachment is by means of another silicon tube 108.

Plant material as used herein refers to any plant or portion thereof, including but not limited to whole plants, including cuttings and rooting cuttings thereof, seedlings, including cuttings and rooted cuttings thereof; tissue cultures, including cultures of roots, shoots, callus or other embryonic tissues, including somatic embryos, and the like, including any portions or explanted cultures thereof; and microshoots from tissue culture. Plant material used in the context of the present invention preferably is or is isolated from, but is not limited to, woody perennials, such as, for example, plants and tissue cultures of hardwoods and conifers. Preferred woody perennials include, but are not limited to sweetgum; sycamore; oak; green ash; cottonwood; loblolly, slash, or radiata pine; black, red, white, sitka, or interior spruce; European, Japanese or Western Larch; and Douglas Fir. More broadly, woody perennials preferably used in the context of the present invention include species of the following genera: Populus, Eucalyptus, Pinus, Acacia, Picea, Larix and Gmelina. Preferred conifers include Pinus spp., Picea spp., and Larix spp., including Douglas Fir. Although preferred embodiments discussed herein include application to the aforementioned trees, the present invention is intended for use with any plant material, including, without any intention of limitation, any herbaceous or woody perennial.

Preferably, the culture conditions used preclude or largely preclude the introduction of fungal or bacterial species other than plant material of the plant of interest and any symbiants, if any, required for growth of the plant material; or if such fingal or bacterial species is introduced that could retard or overgrow the plant material of the plant of interest, then suitable conditions are used that will retard the growth of the undesirable fungal or bacterial species relative to that of the plant material of the plant of interest, The plant material is preferably placed into a chamber on an inert substrate, where the plant material can be exposed to light of varying wavelengths and intensities for defined periods of time. Medium containing nutrients sufficient for growth of the plant material is presented to the plant material by periodically immersing the inert substrate in the medium for a defined residence time as discussed below, thereby placing the plant material in contact with the medium, followed by the substantial removal of the medium from the inert substrate; the remainder of the time, i.e., between the residence times of immersion of the inert substrate in the nutrient medium, the plant material is in contact with the inert substrate and medium that is withheld by surface tension characteristics of the medium on the inert substrate. The inert substrate can be any suitable absorbent or non-absorbent material, and is preferably a non-absorbent material such as, but not limited to, glass, ceramic, stone, plastic; and the substrate can be any suitable shape or size, including spheres, cubes, or random shapes, each having an approximate longest dimension of length or diameter of, for example, from about 1 mm to about 5 mm.

Airflow into the chamber is preferably controlled such that undesired microorganisms are not introduced and the carbon dioxide concentration is held at a preferred level. Accordingly, the airflow into or out of the chamber is screened preferably by a filter having a pore size that precludes or substantially precludes passage of a microbe, such as that of between about 0.2 $\mu$m and 0.45 $\mu$m pore sizes. Similarly, the introduction of medium into or out of the chamber preferably includes sterilization of same prior to entering the chamber and, upon recovery from the chamber, prior to reentry into the chamber. Such sterilization of the medium can be effected by any suitable method, such as, but not limited to filtering, exposure to ozone or ultraviolet light, or heating, such as in an autoclave. It is contemplated, however, that the chamber and medium as recited herein sufficiently retards the growth of undesirable microbes and that, in one embodiment, no sterilization between periods of introducing the nutrient medium into the bioreactor is required.

In a first embodiment, the present invention relates to a method for propagating plant material comprising culturing the plant material in a concentration of carbon dioxide in excess of about 7000 $\mu$l/l, more preferably, in excess of about 7500 $\mu$l/l. Any plant material can be subjected to the inventive method, as noted above; however it is preferred to select plant material that is free or substantially free of contaminating bacteria or other microbes. Such selection can be effected using any method known in the art, such as, for example, incubating the plant material on standard bacterial and/or fungal growth plates, and selecting those specimens of plant material from which no or few deleterious bacteria or other microbes are detected on the growth plates. Preferred ranges of carbon dioxide concentrations used in the context of the present invention are from about 7000 $\mu$l/l to about 50,000 $\mu$l/l; and more preferably, from about 7500 $\mu$l/l to about 30,000 $\mu$l/l. Preferably, the first embodiment includes culturing the plant material in a concentration of carbon dioxide in excess of 7000 $\mu$l/l of carbon dioxide and in the presence of substantially only red light applied for varying time intervals (from seconds to weeks) during a photoperiod of unfiltered light. The photoperiod of the unfiltered light can be for any suitable portion of a day, including continuous illumination. However, preferably, the exposure period is from about 12 to about 20 hours, more preferably from about 14 to about 18 hours, and yet more preferably about 16 hours per day. This photoperiod is then interrupted by exposure to substantially red light for varying time intervals.

The first embodiment preferably includes: (a) introducing the plant material into a chamber that includes the carbon dioxide; and (b) exposing the plant material to pulses of substantially only red light during the photoperiod of unfiltered light. It is further preferred that the first embodiment includes (c) introducing a nutrient medium into the chamber followed by (d) removing the nutrient medium from the chamber. Preferably, the nutrient medium has a pH of between about 4 and about 6. More preferably, the medium has a pH of from about 5 to about 6. The pH can be maintained via use of buffering agents known in the art or by measurements and adjustments over time using, for example, a pH titrant, such as an acid or base. Preferably, the medium is stored in a reservoir connected to the chamber by a conduit. The reservoir can have any suitable dimensions, and can be of any suitable shape, although generally, the reservoir will be a standard sterilizable container capable of holding at least about 500 ml of liquid. The conduit is constructed from any suitable material, the suitability of which is determined by its flexibility, ability to be sterilized, and characteristic of not imparting material into the fluid being conducted by it. Such a suitable material includes polypropylene, polycarbonate, silicon rubber and the like.

The medium used preferably includes nutrients that foster growth of an explanted plant tissue, such as, for example, the macro- and micronutrients set forth in Murashige & Skoog, *Physiol. Plant.*, 15, 473–497 (1962), which are hereinafter referred to as "MS salts." MS salts used in the context of the present invention include suitable concentrations of ammonium nitrate, boric acid, calcium chloride, cobalt chloride, cupric sulfate, $Na_2$-EDTA, ferrous sulfate, magnesium sulfate, manganese sulfate, molybdic acid, potassium iodide, potassium nitrate, potassium phosphate monobasic, sodium nitrate, sodium phosphate monobasic and zinc sulfate. Minimal MS salts used in the context of the present invention preferably include the following as the recited concentration: $NH_4NO_3$ (1650 mg/l); $KNO_3$ (1900 mg/l); $CaCl_2 2H_2O$ (440 mg/l); $MgSO_4 7H_2O$ (370 mg/l); $KH_2PO_4$ (170 mg/l); KI (0.83 mg/l); $H_3BO_3$ (6.3 mg/l); $MnSO_4 4H_2O$ (22.3 mg/l); $ZnSO_4 7H_2O$ (8.6 mg/l); $Na_2MoO_4 2H_2O$ (0.25 mg/l); $CuSO_4 5H_2O$ (0.025 mg/l); $CoSO_4 6H_2O$ (0.025 mg/l); $Na_2EDTA$ (37.3 mg/l); $FeSO_4 7H_2O$ (27.8 mg/l). Additionally, other components can include glycine, glutamine, myo-inositol, nicotinic acid, pyridoxine HCl, sucrose, and thiamine, for example. Such a medium can also include components to cause or foster differentiation or dedifferentiation of the explanted tissues being propagated in the chamber. Such components include, but are not limited to, auxins, cytokinins and abscisic acid. As noted, the medium preferably also is adjusted to a suitable pH range that is preferably between about 4 and about 6. In a preferred embodiment, the nutrient medium includes suitable buffering agents for maintained the preferred pH range. Suitable buffering agents preferably have a pKa between about 4.5 and about 5.5, and include, but are not limited to, citric acid, N-morpholino-ethansulfonic acid, potassium hydrogen phthalate, and benzoic acid.

The chamber in which the plant material is being incubated can be held static with respect to the medium provided to the chamber. In such an embodiment of the invention, no additional medium is added to the reservoir while incubating the plant tissue. Alternatively and preferably, the aforementioned steps (c) and (d) are repeated, such that the residual medium left on the inert substrate and plant material after the medium is removed from the chamber is refreshed periodically. Preferably, the infusion or introduction of medium and removal of same thereafter occurs at about four (4) intervals during a 24 hour period (further described below), with a residence time of the medium in the chamber of between about one (1) and one hundred twenty (120) minutes, more preferably between about fifteen (15) and sixty (60) minutes, yet more preferably between about fifteen (15) and thirty (30) minutes.

The present method preferably further includes: (e) monitoring the pH value of the medium; and (f) adjusting the pH of the medium to maintain the pH between about 4 and about 6. Adjustment of the medium in response to the aforementioned measurements is accomplished by addition of suitable quantities of titrant, i.e., acid or base, as appropriate.

After removal of the nutrient medium from the chamber, an amount of medium remains in the chamber due to surface tension characteristics of and entrainment in the inert substrate, accordingly, the removal is referred to herein as "substantial" removal. The amount remaining preferably does not substantially impede atmospheric contact with the plant material such that adverse effects of impeding transpiration is preferably minimized. To the extent that availability of the medium becomes growth limiting in the intervals between flooding the chamber with medium, then the intervals are shortened accordingly to increase the rate of introducing medium into the chamber. The removal of the nutrient medium allows maximal contact of the cultured plant material with the preferably heightened carbon dioxide concentration of the atmosphere maintained in the chamber.

The medium can contain agents to prevent or retard the growth of bacteria or fungae, such as an antibiotic or antimycotic. Suitable antibiotics include those that retard or prevent the growth of bacteria including, but not limited to carbenecillin, gentamycin, and streptomycin. Suitable antimycotics include those that retard or prevent the growth of yeasts, including but not limited to miconazole (Sigma Chemical Company, St. Louis, Mo.; Cat No. M3512). The antibiotics or antimycetics are included in the medium preferably at a concentration range of from about 25 mg/l to about 1,000 mg/l; more preferably from about 100 mg/l to about 750 mg/l; yet more preferably from about 350 mg/l to about 600 mg/l; most preferably, at about 500 mg/l.

The plant material contained in the chamber is exposed to unfiltered light continually or for photoperiods that are preferably from about twelve (12) to about twenty (20), more preferably from about fourteen (14) to about eighteen (18), and yet more preferably about sixteen (16) continuous or interrupted hours out of every twenty-four (24) hours. Unfiltered light includes natural light, and light from artificial sources which includes all or substantially all of the wavelengths of natural light necessary for plant growth. Pulses of filtered light are included in this exposure, which filtered light can be provided by use of suitable filters applied to a suitable light source. Filters are available from commercial sources, such as Edmund Scientific Company, Barrington, N.J. Various light filters can be used to provide filtered light in the yellow, red, orange, green, blue, indigo and violet ranges of the visible light spectrum. Because of the typically imprecise filtering of inexpensive filters that are useful in the context of the present invention, it is contemplated that, for example, when red light is applied in the present method, that such red light is substantially only red light. By substantially only red light, it is intended that at least about 10% of the visible spectrum that is in the red range is included, more preferably, about 20% of the red range is included, yet more preferably about 50% of the red range is included. Preferably, at least about 50% of the light intensity used to expose the plant material is in the red range; more preferably, at least about 75%, yet more preferably at least about 80%. Pulses of filtered light can vary in intensity, from, for example, about three hundred foot-candles to in excess of ten thousand foot candles. The effects of the invention are preferably achieved with shorter pulses, for example, less than one second, of high-intensity light, for example, greater than 1,000 foot candles, or longer pulses, for example, about two (2) weeks, of low intensity light, for example, 500 foot candles. One skilled in the art can determine without undue experimentation the optimal duration of pulses of a particular light intensity and wave length. Repeated pulses can occur at regular intervals or at irregular intervals.

In a second embodiment, the present invention preferably relates to a method for propagating plant material by exposure to concentrations of carbon dioxide in excess of 1000 $\mu l/l$. The concentration of the carbon dioxide preferably ranges from in excess of 1000 $\mu l/l$ to about 50,000 $\mu l/l$; more preferably from about 3500 $\mu l/l$ to about 50,000 $\mu l/l$; yet more preferably from about 7000 $\mu l/l$ to about 50,000 $\mu l/l$; even more preferably from about 7500 $\mu l/l$ to about 30,000 $\mu l/l$.

The second embodiment further includes exposing the plant material to filtered light applied for varying time intervals (seconds to weeks) during a photoperiod of unfiltered light.

The second embodiment is implemented preferably in the context of the chamber recited above with respect to the first embodiment. The container can accommodate a wide variety of plant material including but not limited to (a) the plant material in a chamber as recited above with respect to the first embodiment, (b) plant tissue cultures on semi-solid or liquid media, and (c) cuttings, microcuttings, or seedlings in soil or soilless media under non-aseptic conditions.

Preferably, the second embodiment relates to a method for propagating plant material including introducing the plant material into a chamber and therein culturing the plant material in excess of 1000 $\mu l/l$ concentration of carbon dioxide, and exposing the plant material to pulses of substantially only red light during a photoperiod of unfiltered light.

EXAMPLE 1

This example sets forth methods used for obtaining various plant tissues for use in illustrating the present invention.

Plant cultures and media used in illustrating the present invention included the following: Seeds of carrot (*Daucus carota* L. cv. 'Danver's Half Long'), kale (*Brassica oleracea* L. cv. unknown), lettuce (*Lactuca sativa* L. cv. 'Grand Rapids Lettuce'), radish (*Raphanus sativus* L. cv. 'Scarlet Globe'), tomato (*Lycopersicum esculentum* L. cv. 'Cherry Red'), loblolly pine (*Pinus taeda*) and thyme were surface sterilized in a 2.6% sodium hypochlorite solution (containing 2 drops of Tween-20 emulsifier per 100 ml solution) for 20 minutes and placed on the surface of basal medium ("BM"). Two seeds were cultured per vessel. Stock plantlets of citrus (*Citrus macrophylla* L. cv. unknown) were maintained as proliferating axillary buds on BM as source of shoots. A single 2-cm long shoot was cultured per vessel. The BM consisted of MS salts (Murashigi & Skoog, supra) plus (per liter): 0.5 mg thiamine HCl, 100 mg i-inositol, and 10 g agar (Difco Laboratories, Detroit, Mich.). BM with 0 and 30 g liter$^{-1}$ sucrose was tested. The pH was adjusted to 5.7±0.1 with 0.1 N HCl or NaOH before the addition of agar, then melted and dispensed in 25-ml aliquots into 25 150 mm borosilicate glass culture tubes and capped with transparent polypropylene closures (Sigma Chemical Co., St. Louis, Mo.). Medium was autoclaved for 15 minutes at 1.05 kg cm$^2$ at 121° C. and agar medium was then slanted at a 45° angle while cooling.

Sweetgum (*Liquidambar styraciflua*) shoot cultures were also used in illustrating the present invention, and were established from mature trees by the method of Sutter & Barker, *Plant Cell, Tissue and Organ Culture*, 5, 13–21 (1985).

EXAMPLE 2

This example presents plant tissue culture experiments conducted to investigate the effects on growth of plant tissue of varying concentrations of carbon dioxide in the atmosphere and sucrose in the medium, using a carbon dioxide flow system.

Figure 2:
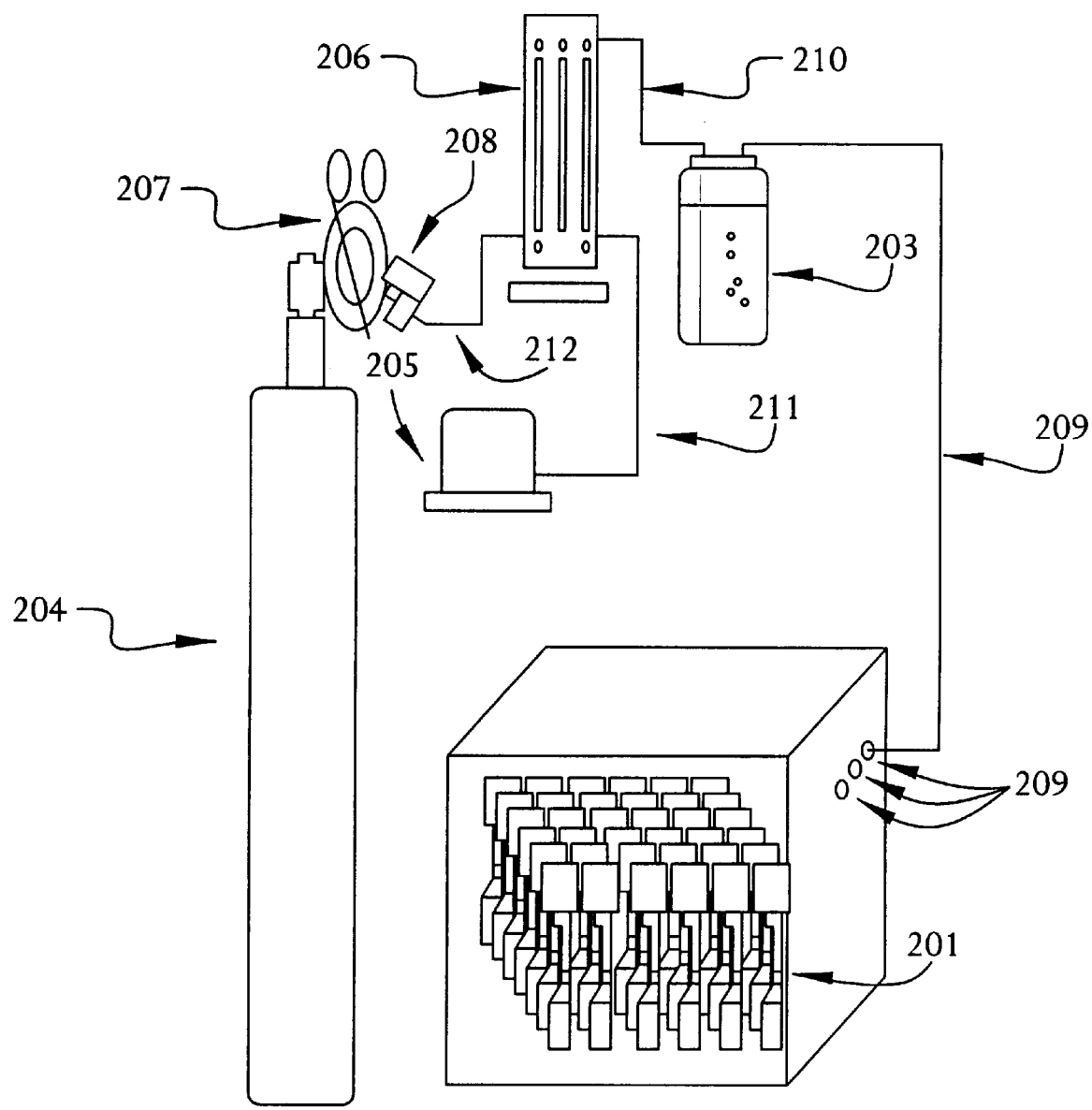
FIG. 2 is a diagram of a device to deliver $CO_2$ to tissue cultures or the bioreactor.
Figure 3A:
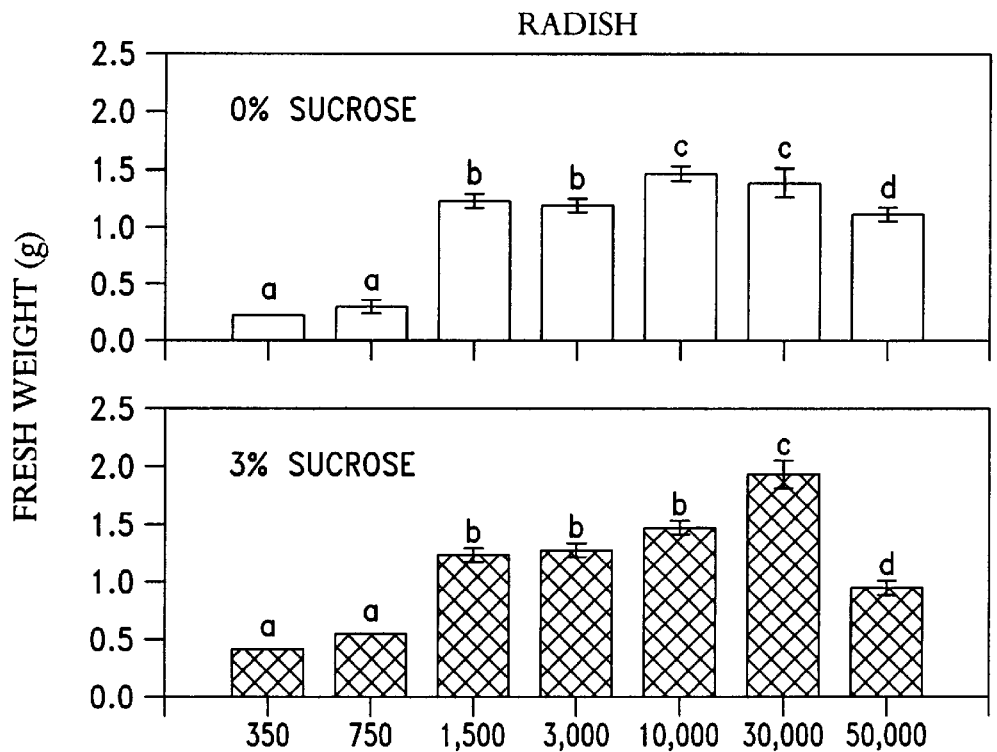
FIGS. 3A–3E displays graphs of growth responses of several plants to various levels of carbon dioxide in vitro after 8 weeks in culture.
Figure 3B:
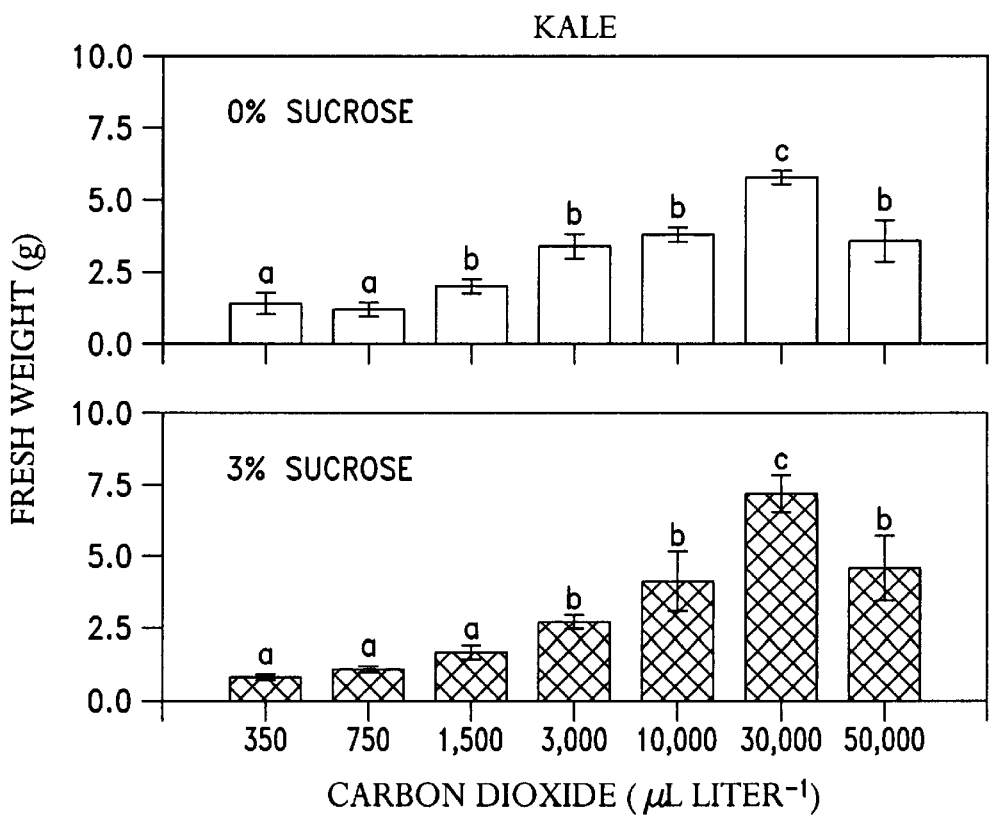
Figure 3C:
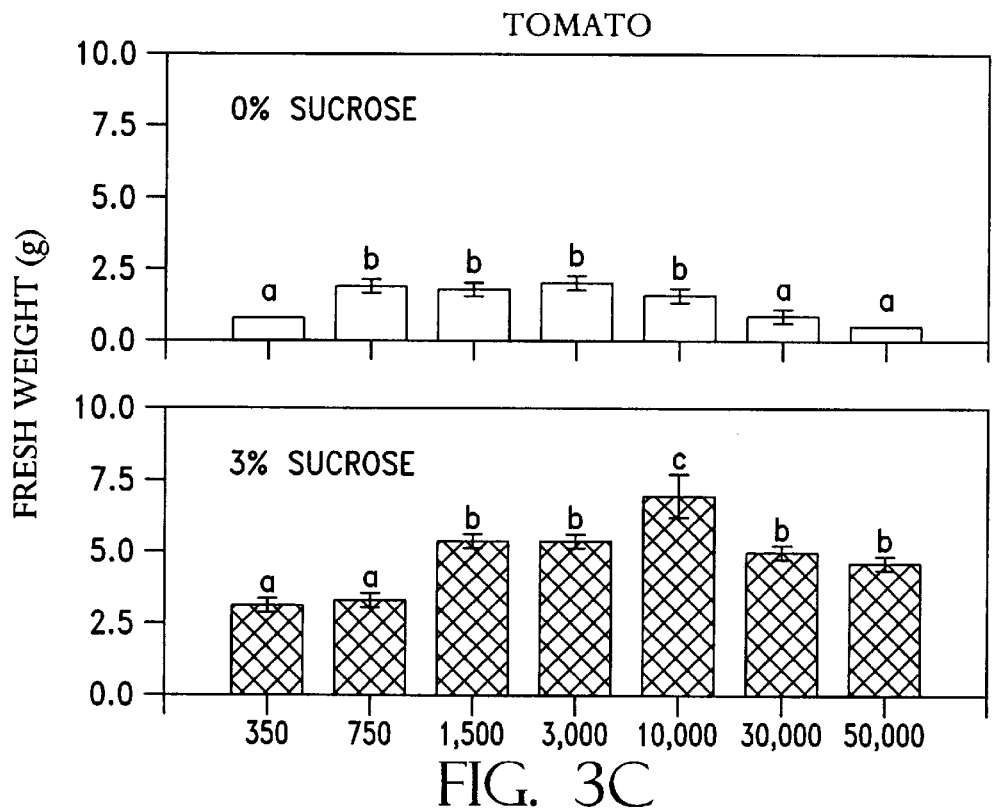
Figure 3D:
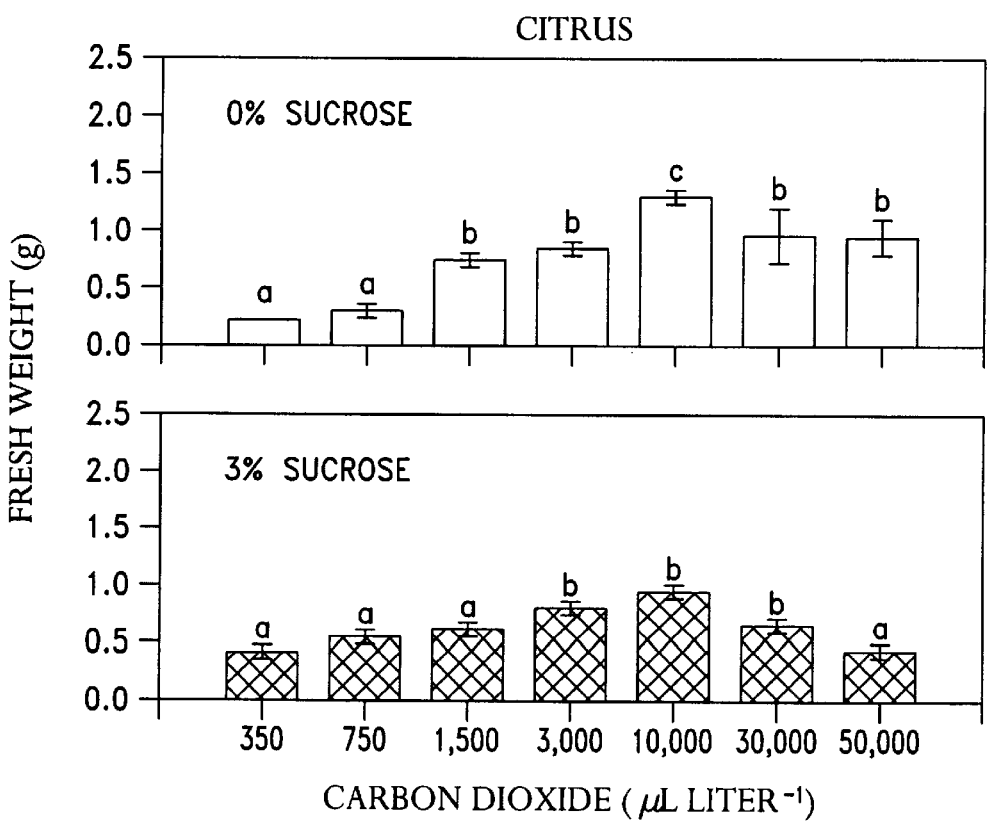
Figure 3E:
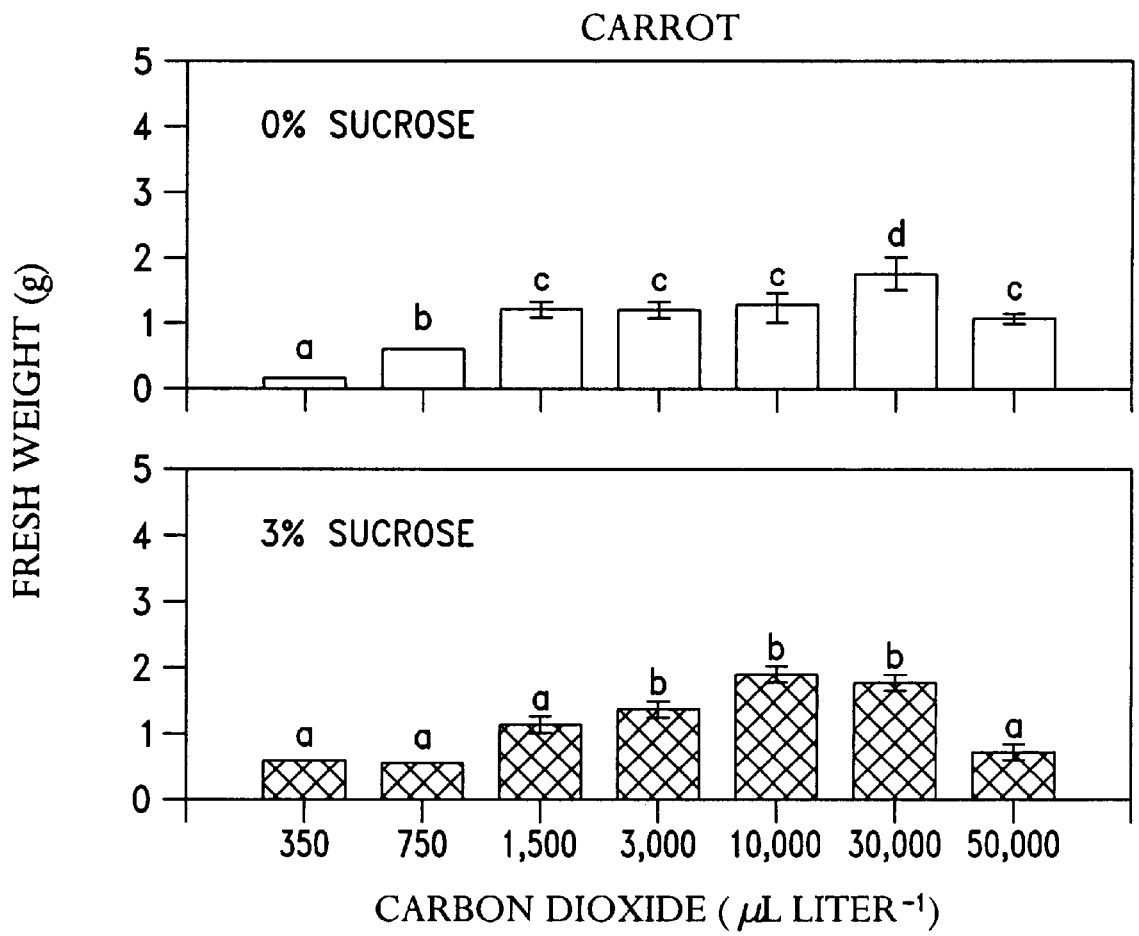
Figure 4A:
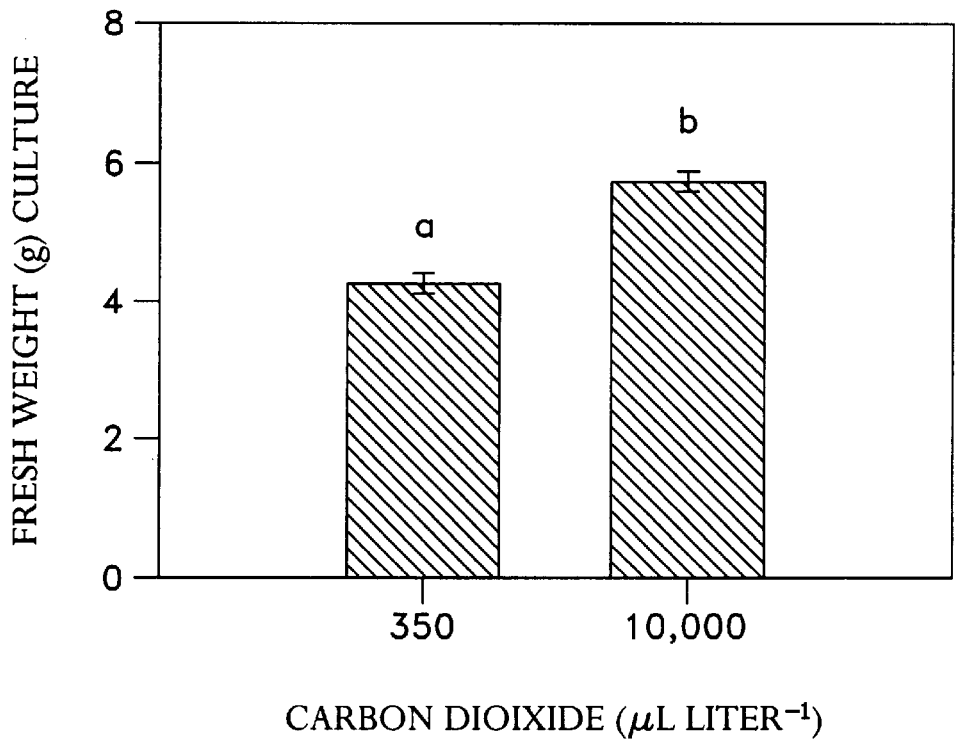
FIGS. 4A–4D displays bar graphs that are directed to the influence of carbon dioxide on the growth of sweetgum cultures.
Figure 4B:
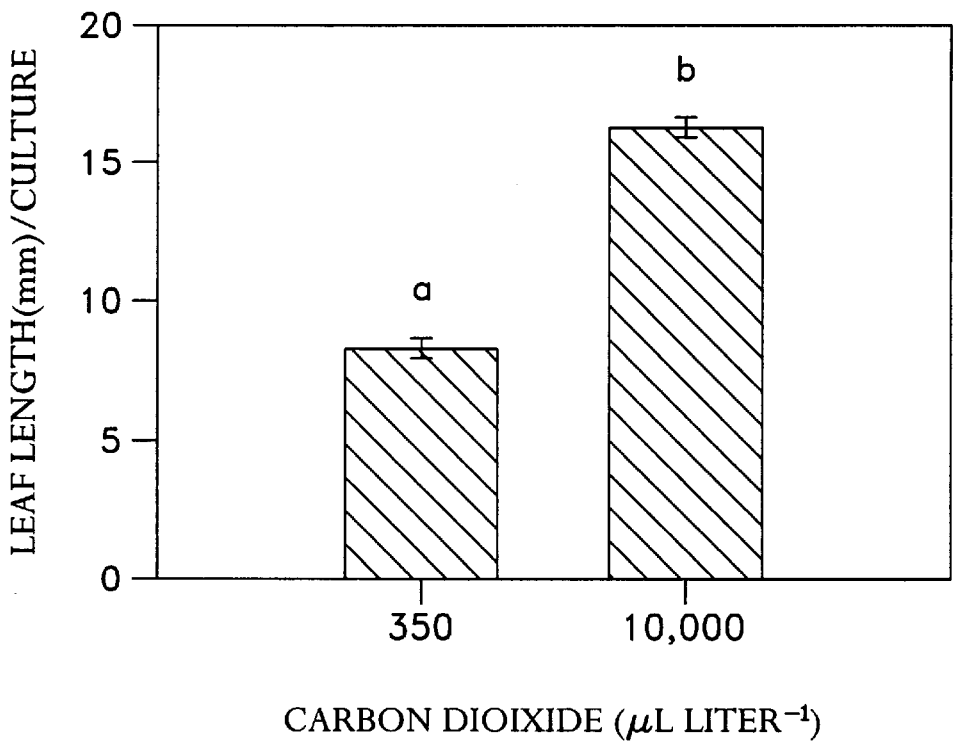
Figure 4C:
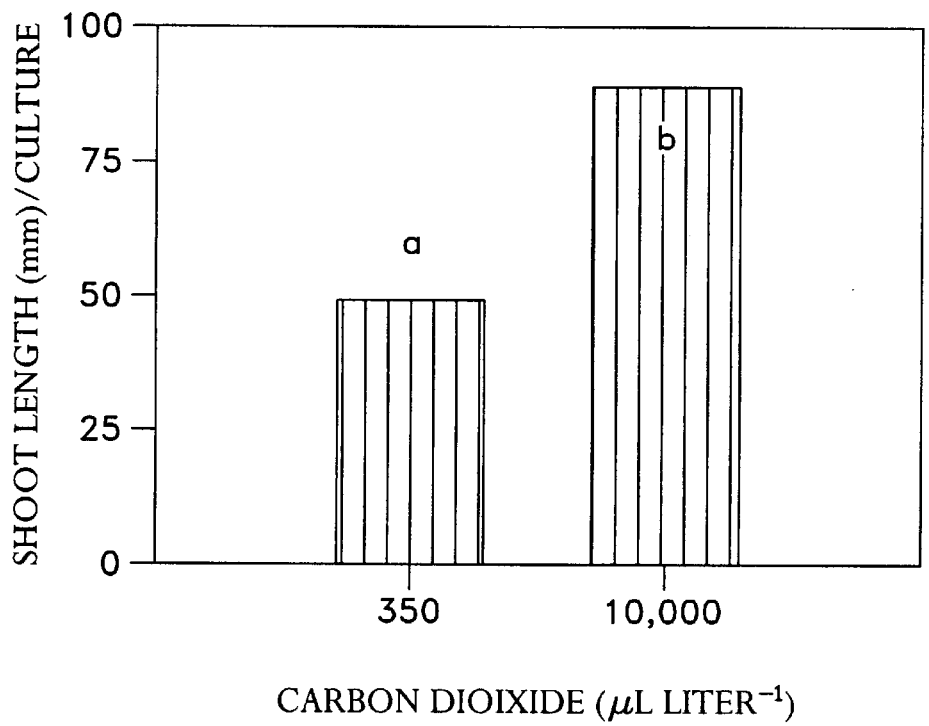
Figure 4D:
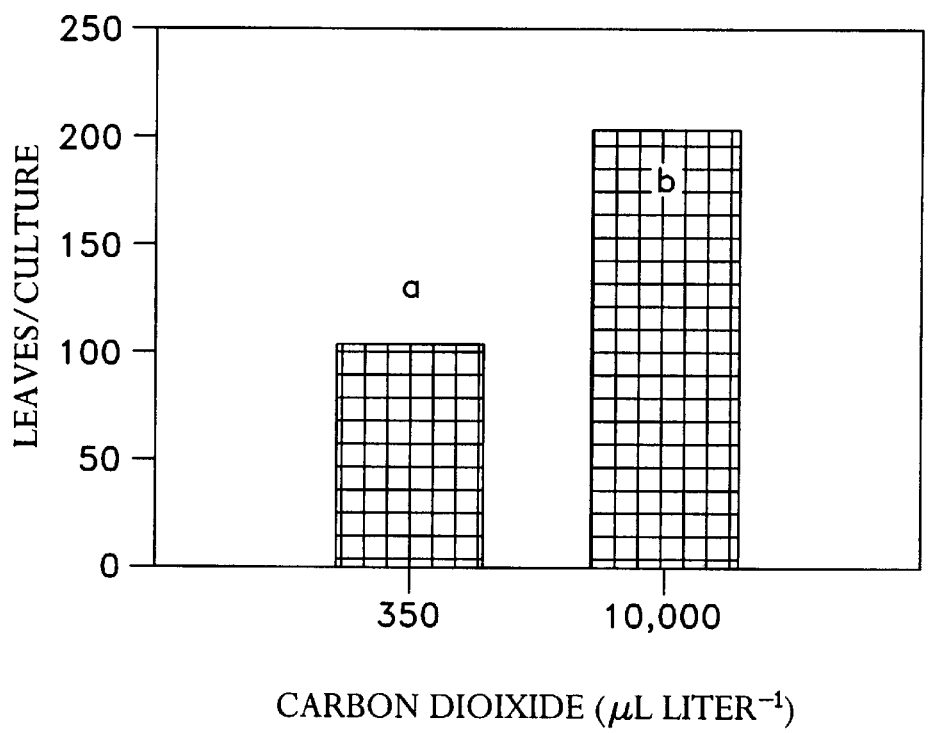

A $CO_2$ flow testing chamber 201 was constructed from a 94.5-liter transparent polycarbonate Carb-X tote box and lid (Consolidated Plastics, Twinsburg, Ohio) (45 cm width×65 cm length×37.5 cm depth; 94.5-liter capacity) (FIG. 2). A silicone tape gasket (112 cm long×6.3 mm wide×3.2 mm thick) (Furon, New Haven, Conn.) was attached to the lid. The box was modified by mounting three polypropylene spigots 202 to allow for the inflow and evaction of gases. Two 0.45 μm air vents (Gelman Science, Ann Arbor, Mich.) were attached to two of these spigots 202 with silicone tubing to 1.6-mm inner diameter female barbed fittings (Ark-Plas Products, Flippin, Ark.). The box and lid were clamped with 12 equally spaced stationary binding clips (50 mm long). The $CO_2$ testing chamber was attached to a water reservoir 203 with silicon rubber tubing 209. The water reservoir 203 consisted of a 2.25-liter polycarbonate bottle containing 1.5-liter distilled water. Carbon dioxide was provided by gas cylinder 204 (National Welding Supply Company, Inc., Bloomington, Ill.) rated 99.8% pure and was mixed with room air flow produced by an aquarium pump 205 (Whisper 1000, Carolina Biological Supply Company, Burlington, N.C.) with a flow meter 206 (Cole Parmer Instrument Co., Niles, Ill.) to provide 350, 750, 1,500, 3,000, 10,000, 30,000, and 50,000 μL liters$^{-1}$. The $CO^2$ gas cylinder 204 was connected to a flow regulator 207 and a solenoid valve 208; all interconnections between components were effected using silicon tubes 209–212, as shown in FIG. 2. Carbon dioxide ranges above 10,000 μL liter$^{-1}$ were adjusted using a Model #3000 LIRA infrared Gas Analyzer (Mine Safety Appliances Company, Pittsburgh, Penn.) and $CO_2$ ranges$\geq$3,000 μL liter$^{-1}$ adjusted with the aid of a LI-6262 Li-Cor $CO_2/H_2O$ infrared gas analyzer (Li-Cor, Inc., Lincoln, Neb.). The $CO_2$ and air streams were added at about 1,500 ml min$^{-1}$ for 16 hours photoperiod. Control cultures were given a stream of room air generated by the aquarium pump 205 and hydrated with the water reservoir 203. In flow experiments, air flow rates were adjusted with gang value and flow meters to 250, 500, 1,000, 1,500 and 2,000 ml min$^{-1}$.

Carrot, kale, radish and tomato seeds (two per 25×150 mm tube) and citrus microshoots were planted in BM containing 0 or 3.0% sucrose and grown under 350, 750, 1,500, 3,000, 10,000, 30,000 and 50,000 μl liter$^{-1}$ $CO_2$ within 94-liter transparent containers as shown in FIG. 2. Cultures were grown in a culture room maintained at 25° C.±1° C. and employed a photoperiod of 16 hr light/8 hr. dark. Light was supplied by a combination of fluorescent tubes (Coolwhite), metal-halide and incandescent lights at a photosynthetic photon flux density (PPFD) of 260 μE m$^{-2}$ s$^{-1}$ at the vessel periphery.

Ten to twenty replicates were planted originally, and experiments were repeated at least twice. After 8 weeks of incubation, data on culture fresh weight, shoot height, leaf number, leaf length, leaf width, root number, and root length were recorded and analyzed with Student-Newman-Keuls multiple range test (P<0.1) when appropriate. Fresh weight data are reported in FIG. 3. Columns in the same sucrose concentration with the same letter in FIG. 3 were not significantly different.

For radish and citrus, increasing the $CO_2$ concentration to 1,500 μL/l was beneficial to growth regardless of the sucrose concentration. For carrot, kale and tomato, high concentrations of $CO_2$ aided growth, but the optimum concentration of $CO_2$ was dependent on the sucrose concentration. Optimum concentration of $CO_2$ appeared to exist where above or below this concentration less growth (i.e. fresh weight) occurs. For example, citrus shoots grown in 0% sucrose exhibit maximum growth at the 10,000 μL liter$^{-1}$ $CO_2$ level while kale seedlings grown in 0% sucrose exhibit maximum growth at the 30,000 μL liter$^{-1}$ $CO_2$ level. The optimum $CO_2$ level varied somewhat among species and media employed but generally 3,000 to 30,000 μL liter$^{-1}$ $CO_2$ levels were found to give the largest fresh weight increases (FIG. 3). Carrot exhibited maximum fresh weight increase of 9.5-fold on BM without sucrose with 30,000 μL liter$^{-1}$ $CO_2$; while on BM with sucrose, a maximum fresh weight of only 1.7-fold occurred with 10,000 μL liter$^{-1}$ $CO_2$. Similarly, kale plantlets exhibited their maximum fresh weight response, a 6.5-fold increase, on BM without sucrose on 30,000 μL liter$^{-1}$ $CO_2$; while on BM with sucrose only a 1.7-fold increase in fresh weight occurred on 3,000 μL liter$^{-1}$ $CO_2$. Citrus shoots exhibited a maximum fresh weight increase of 4.7-fold on BM without sucrose with 10,000 μL liter$^{-1}$ $CO_2$ but on BM with sucrose only a maximum of 1.3-fold increase with 10,000 μL liter$^{-1}$ $CO_2$. Radish plantlets exhibited a maximum fresh weight increase of 6.3-fold on BM without sucrose with 3,000 μL liter$^{-1}$ $CO_2$. Tomato plantlets exhibited maximum fresh weight increase of 0.8 fold on BM without sucrose with 3,000 μL liter$^{-1}$ $CO_2$ and a 1.2-fold on BM with sucrose with 10,000 μL liter$^{-1}$ $CO_2$.

EXAMPLE 3

This example illustrates in influence of carbon dioxide treatments on the growth of sweetgum shoot cultures.

Sweetgum shoot cultures were grown in agar medium (containing 3% sucrose) as set forth in Example 1, in the presence of 350 μl/l or 10,000 μl carbon dioxide using the carbon dioxide delivery mechanism diagrammed in FIG. 2. After 8 weeks of growth under the specified carbon dioxide concentration, the sweetgum cultures were measured with respect to (1) leaf length in millimeters per culture, (2) fresh weight in grams per culture, (3) shoot length in millimeters per culture, and (4) number of leaves per culture, which data are presented graphically in FIG. 4.

As seen in FIG. 4, each parameter measured is significantly greater for the high carbon dioxide exposed culture compared to the ambient atmosphere control. Both leaf length and shoot length doubled, number of leaves and fresh weight increased by nearly two-thirds and one-third, respectively. Exposure to high concentration $CO_2$ clearly benefited growth.

EXAMPLE 4

This example sets forth results of an experiment that tested the effect of varying wavelengths of light on the growth of loblolly pine seedlings.

The effect of red, blue, green, yellow, orange, and white or natural light was tested on 200 mm high loblolly pine seedlings. The results are shown in Table 1, wherein R stands for red filter, Y stands for yellow filter, O stands for orange filter, N stands for natural sunlight, B stands for blue light; G stands for green filter, S stands for 1 shade cloth and D stands for dark conditions only. These filtered light sources were tested for various durations and combinations to determine their optimum effectiveness (see Table 1). No beneficial difference in growth of these seedlings was observed for any of the tests conducted except for those seedlings subjected to treatment #21 (exposure to red filtered light for 4 weeks followed by natural light). Continuous exposure to any other light filters did not give any better results than filter alterations (i.e. filter treatment followed by natural light).

TABLE 1

Filtered light regimens used with loblolly pine seedlings.

| Week # | Original | 2 | 4 | 6 | 8 | 12 | # |
|---|---|---|---|---|---|---|---|
| 1 | O | N | N | N | N | N | 10 |
| 2 | O | O | N | N | N | N | 10 |
| 3 | O | O | O | N | N | N | 10 |
| 4 | O | O | O | O | N | N | 10 |
| 5 | O | O | O | O | O | O | 10 |
| 6 | Y | N | N | N | N | N | 10 |
| 7 | Y | Y | N | N | N | N | 10 |
| 8 | Y | Y | Y | N | N | N | 10 |
| 9 | Y | Y | Y | Y | Y | Y | 10 |
| 10 | G | N | N | N | N | N | 10 |
| 11 | G | G | N | N | N | N | 10 |
| 12 | G | G | G | N | N | N | 10 |
| 13 | G | G | G | G | G | G | 10 |
| 14 | B | N | N | N | N | N | 10 |
| 15 | B | B | N | N | N | N | 10 |
| 16 | B | B | B | N | N | N | 10 |
| 17 | B | B | B | B | N | N | 10 |
| 18 | B | B | B | B | B | N | 10 |
| 19 | B | B | B | B | B | B | 10 |
| 20 | R | N | N | N | N | N | 10 |
| 21 | R | R | N | N | N | N | 10 |
| 22 | R | R | R | N | N | N | 10 |
| 23 | R | R | R | R | N | N | 10 |
| 24 | R | R | R | R | R | N | 10 |
| 25 | R | R | R | R | R | R | 10 |
| 26 | N | S | N | S | N | S | 10 |
| 27 | S | N | S | N | S | N | 10 |
| 28 | S | N | N | N | N | N | 10 |
| 29 | D | N | N | N | N | N | 10 |
| 30 | D | D | N | N | N | N | 10 |
| 31 | D | N | D | N | D | N | 10 |
| 32 | N | R | N | R | N | R | 10 |
| 33 | N | B | N | B | N | B | 10 |
| 34 | N | O | N | O | N | O | 10 |
| 35 | N | Y | N | Y | N | Y | 10 |
| 36 | N | N | N | N | N | N | 10 |

EXAMPLE 5

This example sets forth results of an experiment that tested the effect of ultra-high carbon dioxide levels on growth of loblolly pine seedlings.

Figure 5A:
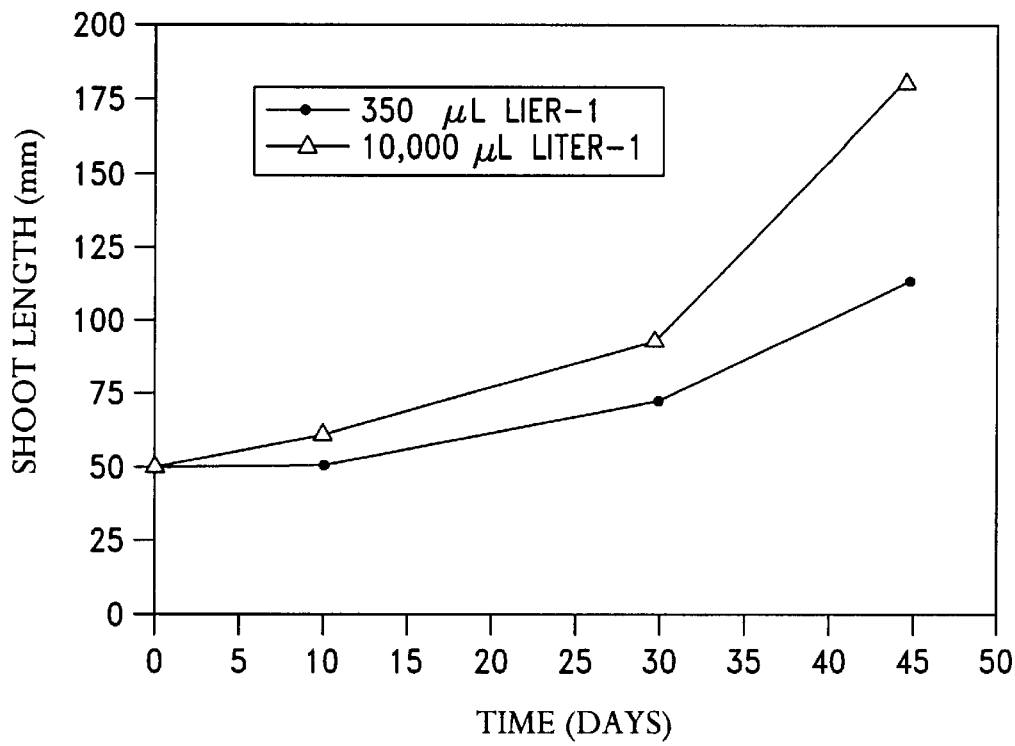
FIGS. 5A and 5B displays graphs that report the influence of high carbon dioxide on pine seedlings over a 45 day period.
Figure 5B:
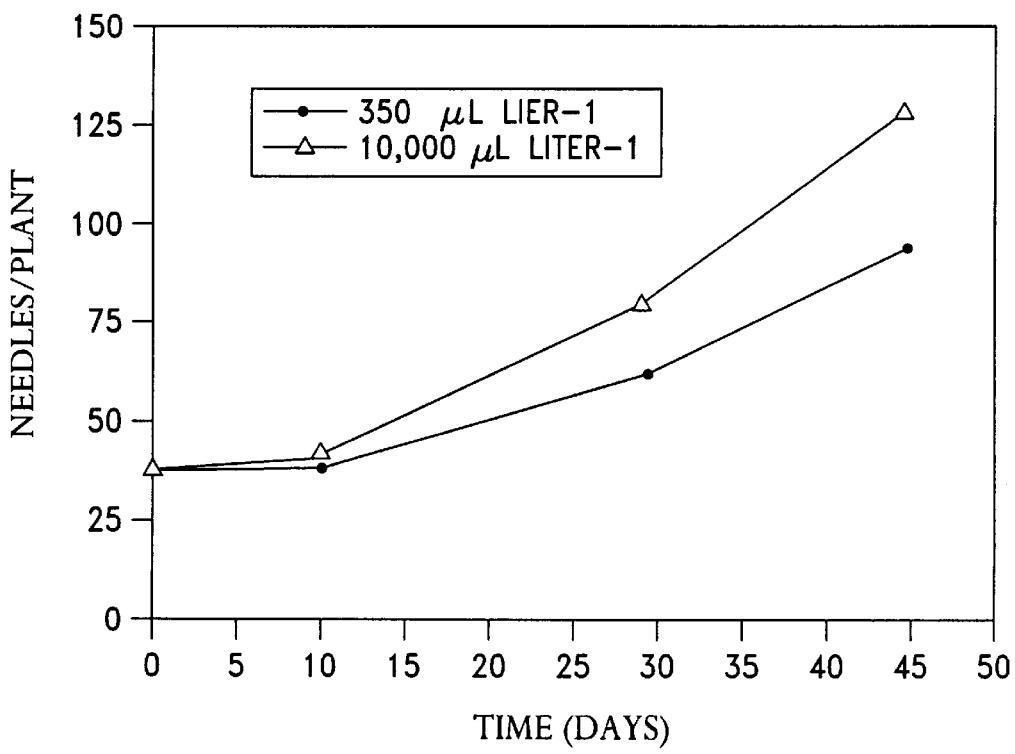
Figure 6A:
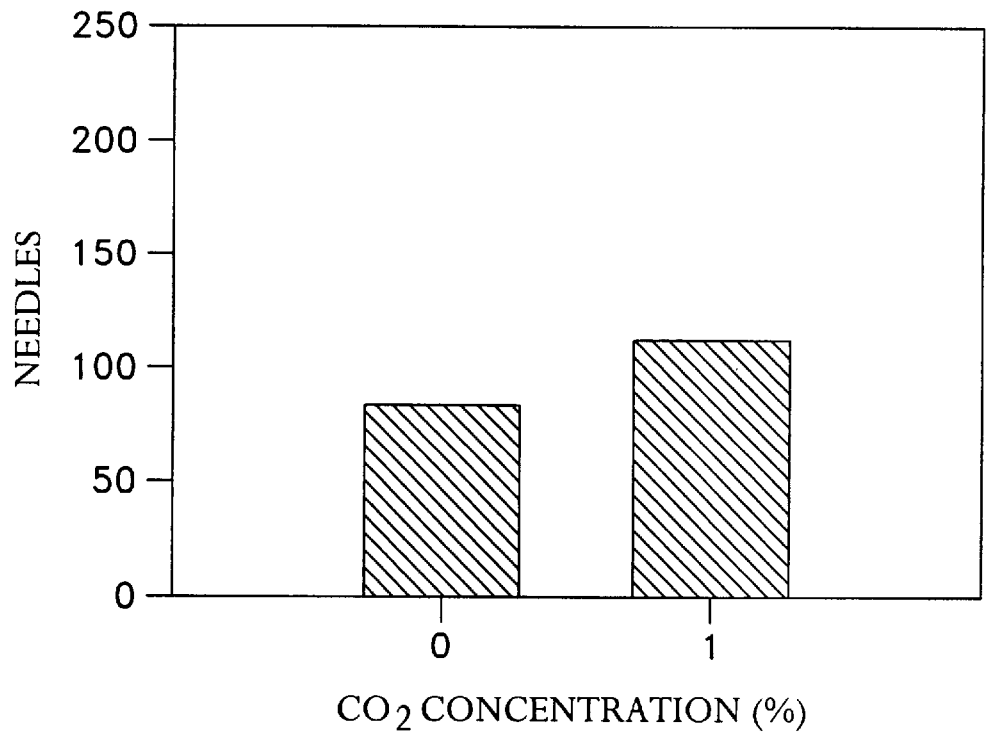
FIGS. 6A–6F displays bar graphs of the influence of ultra-high levels of carbon dioxide on various growth parameters of pine seedlings after 45 days of treatment.
Figure 6B:
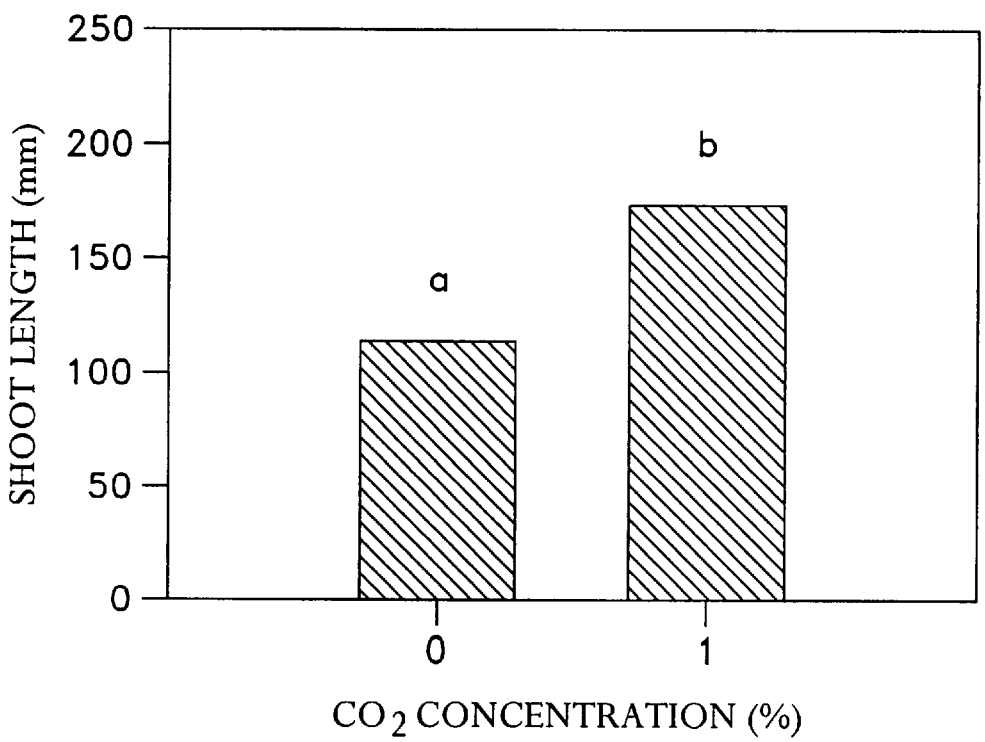
Figure 6C:
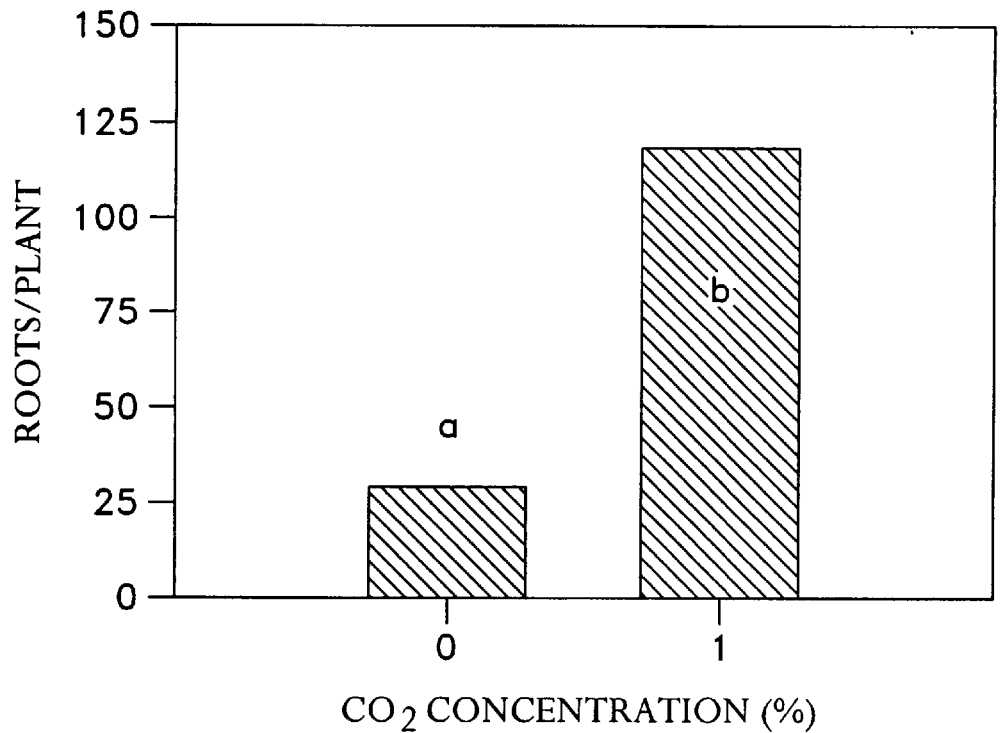
Figure 6D:
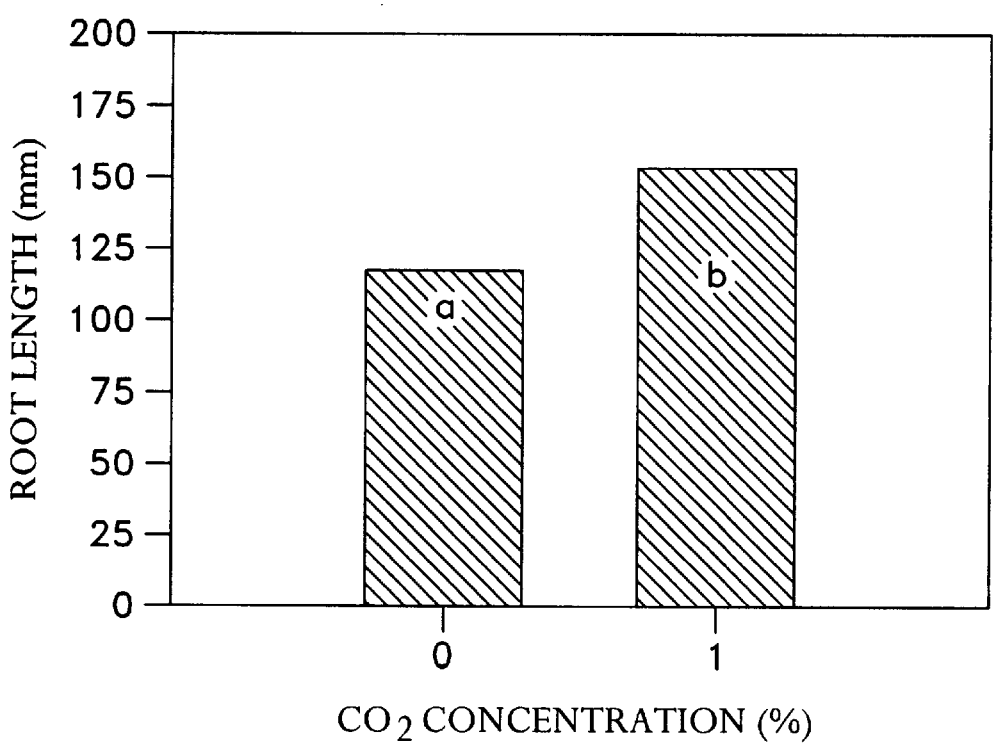
Figure 6E:
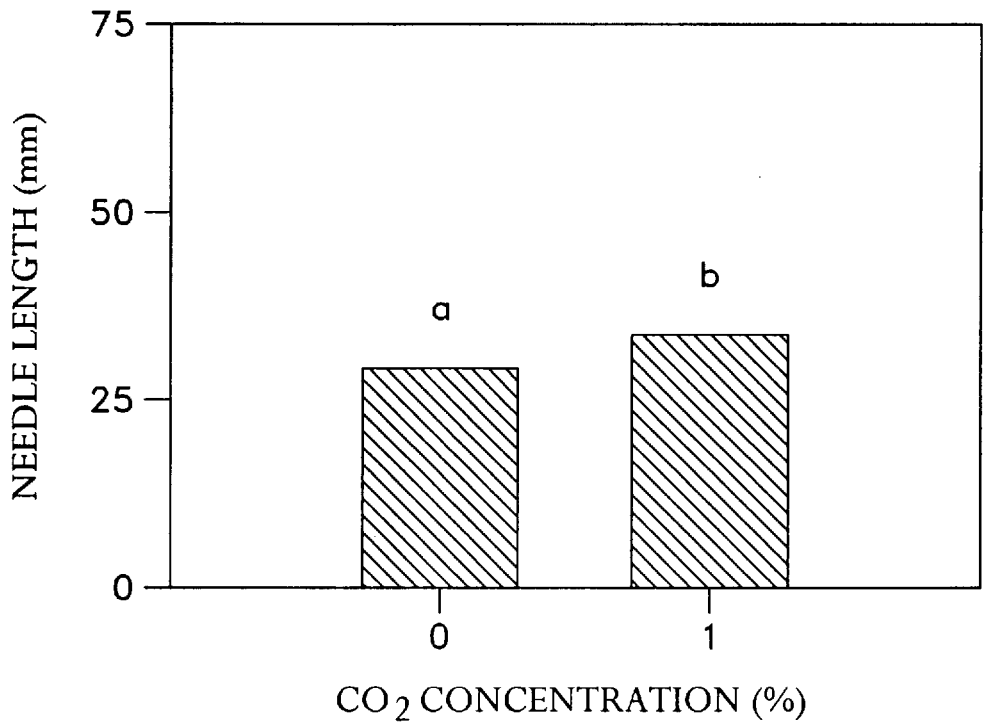
Figure 6F:
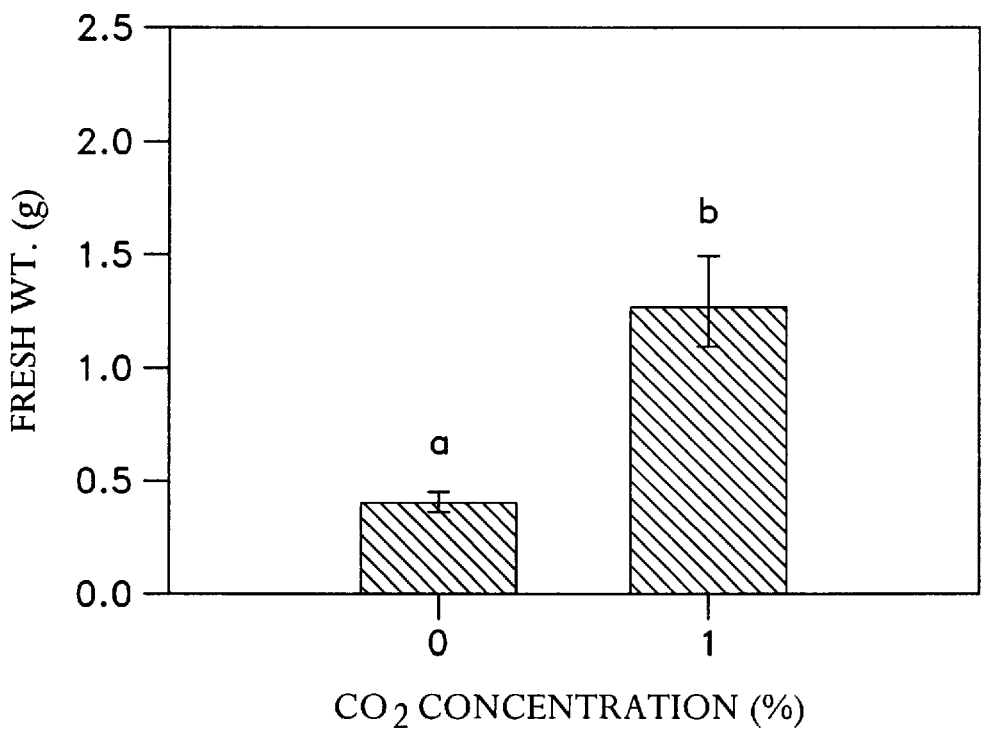

The flow-through $CO_2$ system of FIG. 2 set forth in Example 2 was used to glow loblolly pine seedlings in soil under ultra-high carbon dioxide concentrations, with the variation that low humidity air was used and the air within the chamber was stirred with miniature electrical fans positioned in the $CO_2$ chamber. Using the lowered humidity $CO_2$ chambers, pine seedlings were grown in several ultra-high $CO_2$ environments and exhibited substantially better results than without high $CO_2$. Pine seedlings, ~50–55 mm in height, were grown in 350 and 10,000 $\mu L$ $CO_2$ liter$^{-1}$ for 45 days. Results of this experiment are presented in FIGS. 5 and 6. The benefit of the $CO_2$ appears to be strongest after 30 days of treatment, as shown in FIG. 4, where the curves indicate increasing growth with respect to needles per plant and shoot length. The upper panel of FIG. 5 is a graph of shoot length measured in millimeters over time of the enhanced carbon dioxide treatment; the lower panel of FIG. 5 is a graph of needles per plant over the same time course. As shown in FIG. 6, which is a series of bar graphs comparing the influence of null versus ultra-high levels (0 versus 1%; 1% is equivalent to 10,000 $\mu l/l$ carbon dioxide) of carbon dioxide on various growth parameters of pine seedlings after 45 days of treatment, fresh weight and roots/plant increase dramatically, 223.7% and 285%, respectively, when grown in the 10,000 $\mu L$ $CO_2$ liter$^{-1}$ (i.e., 1% $CO_2$) environment. In addition, number of needles/plant (38.3%), needle length (18.7%), root length (32.2%), and shoot length (59.6%) also increased by the percentages noted parenthetically.

EXAMPLE 6

This example sets forth results of an experiment that tested the effect of combining ultra-high carbon dioxide levels with varying the wavelength of light on growth of loblolly pine seedlings.

Figure 7:
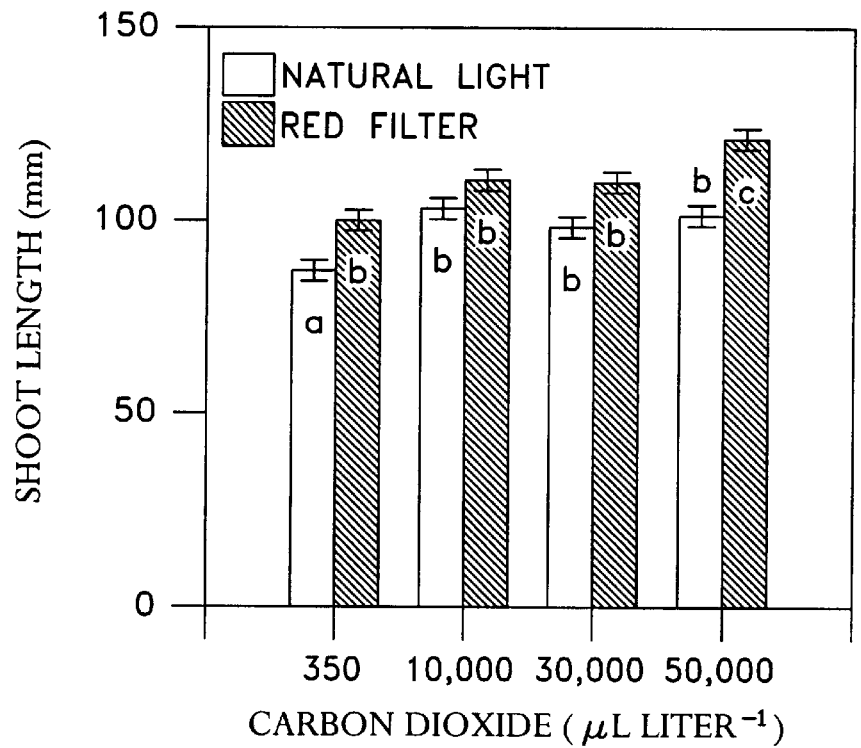
FIG. 7 displays bar graphs of the influence of ultra-high levels of carbon dioxide and red filters on the growth of pine seedlings after 20 days of treatment.
Figure 7:
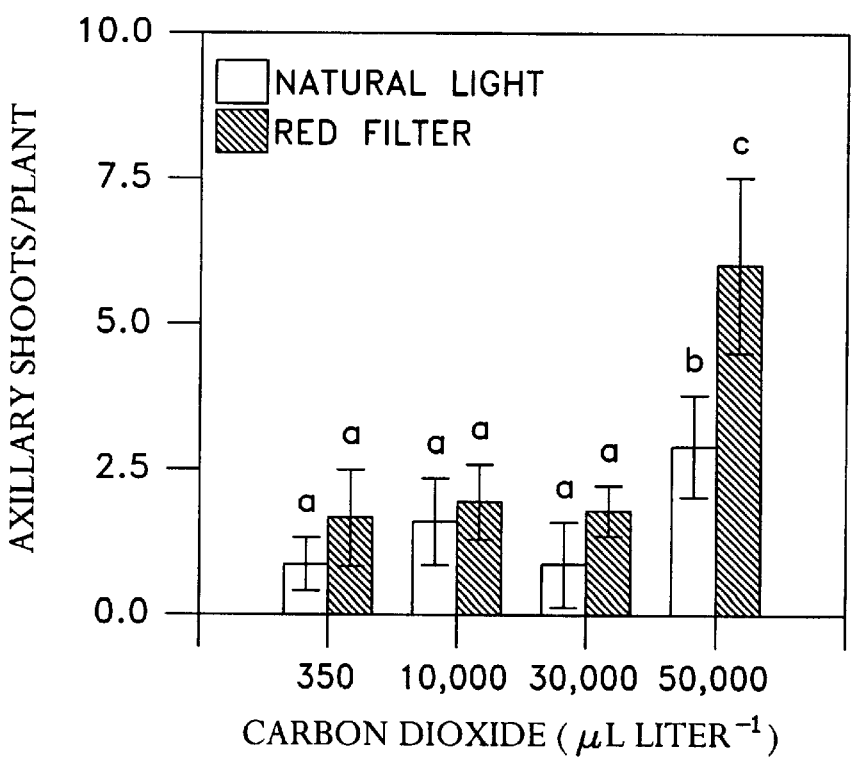

Using the carbon dioxide flow chamber described in Example 5, several ultra-high levels of $CO_2$ were employed with and without use of red filter on ~85 mm high pine seedlings. The red filter was employed since it was found to stimulate growth in the older 200 mm tall seedlings. The results are portrayed in FIG. 7, where the upper panel shows the influence of $CO_2$ on shoot length and the lower panel shows the influence of $CO_2$ on axillary shooting, where the diagonally lined bars represent the results from inclusion of the aforementioned red filter and the blank bars represent the results from inclusion of normal light. As shown in FIG. 7, the high concentration of $CO_2$ stimulated pine shoot length for all ultra-high $CO_2$ levels tested. Red light similarly stimulated shoot length growth and in every case a synergistic response was found coupling red light and ultra-high $CO_2$ concentrations. Further, axillary shooting from the relatively small pine plantlets was substantially enhanced using 50,000 $\mu L$ $CO_2$ liter$^{-1}$ and a red filter.

EXAMPLE 7

This example illustrates the response of sweetgum sterile shoot cultures to various culture environments.

Sweetgum shoot cultures were prepared in accordance with Example 1 and grown in presence of based medium, i.e., the minimal MS salts set forth above. Growth was measured with respect to fresh weights of cultured tissue and shoots per cultures. The cultures were grown (1) on solid agar; (2) in liquid media; (3) in the bioreactor of the present invention, wherein the cultured tissue was placed on glass beads and soaked for 15 minutes each time with the MS salts once, twice or four times per day; (4) in the bioreactor just recited with exposure of air only; or (5) in the bioreactor just recited with exposure of a 10,000 $\mu l/l$ concentration of carbon dioxide.

Figure 8:
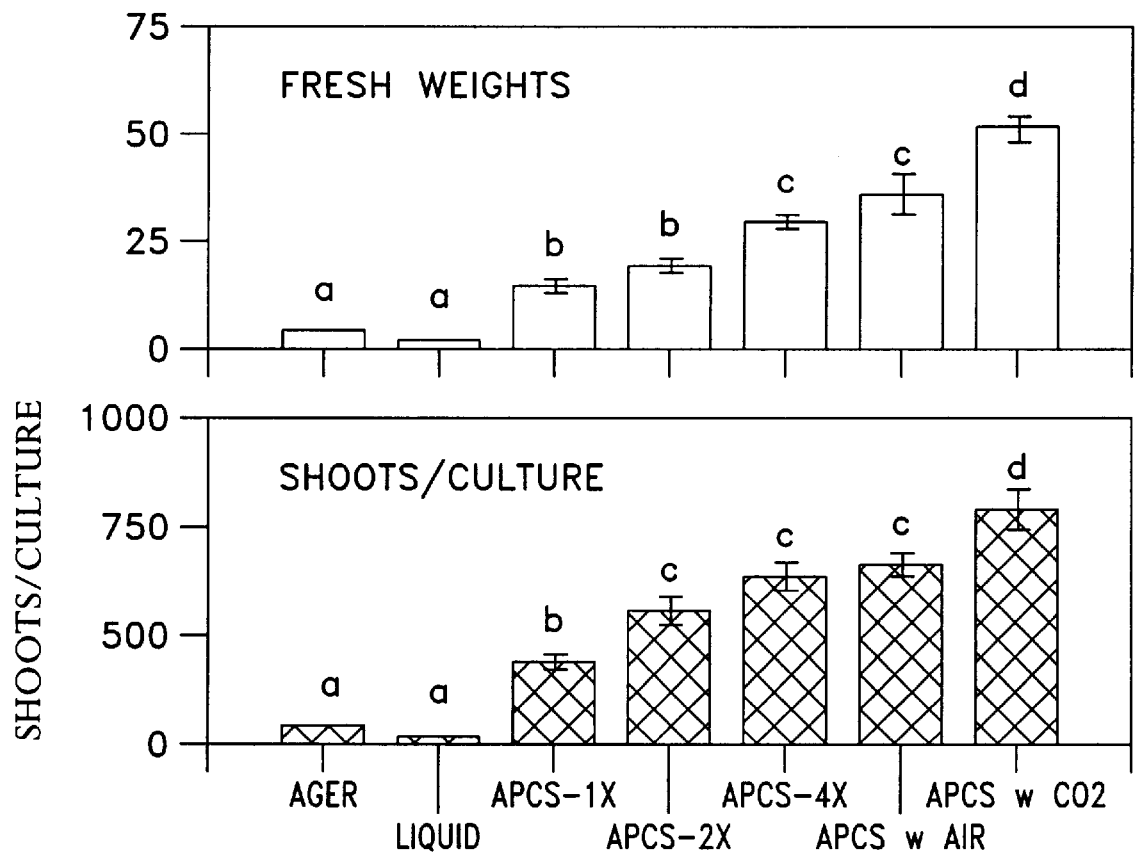
FIG. 8 displays bar graphs that demonstrate the response of sweetgum sterile shoot cultures on various culturing procedures.
Figure 9:
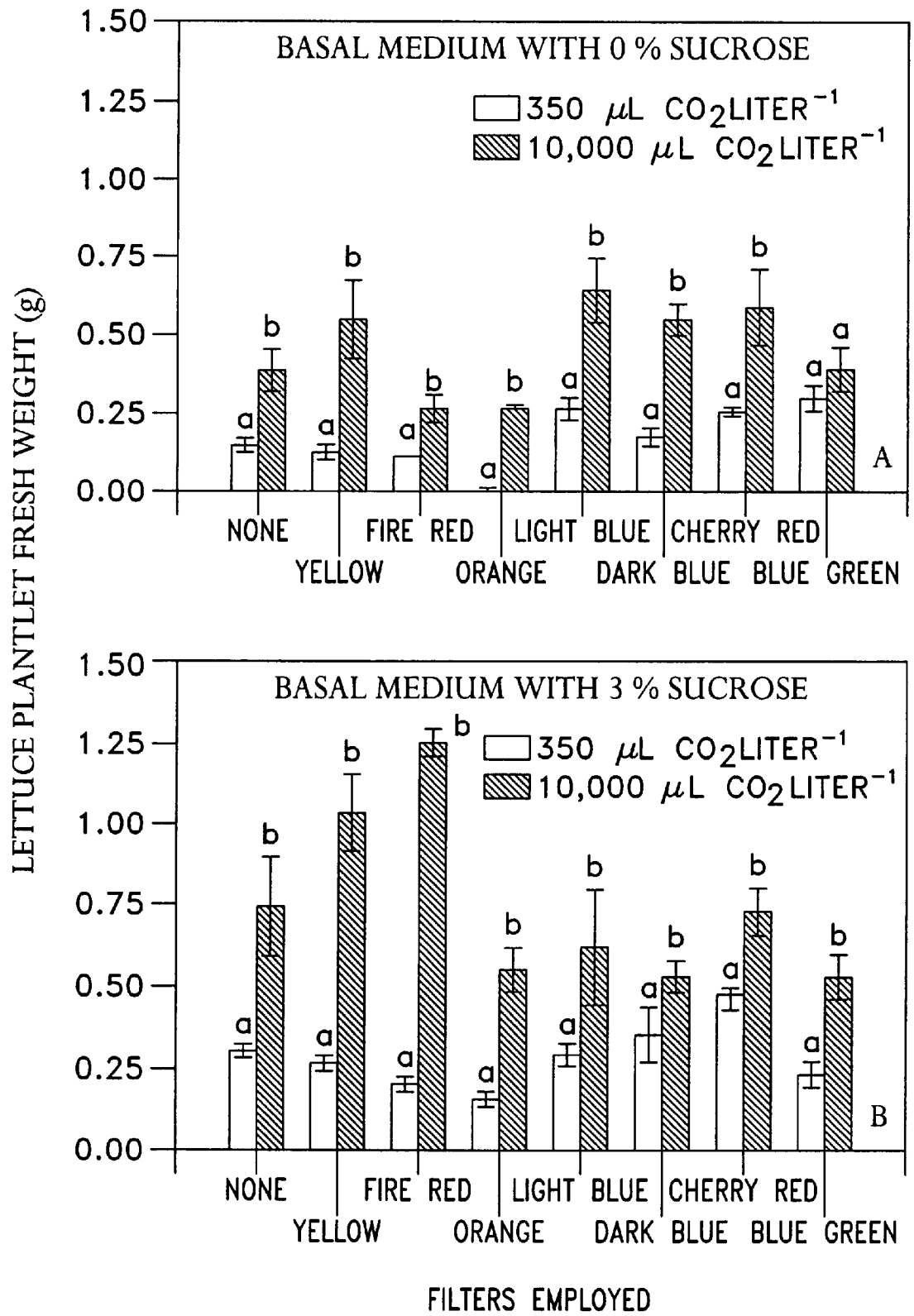
FIGS. 9A–9B display bar graphs that illustrate the effect on lettuce plantlet fresh weight of light color, with and without exposure to 10,000 $\mu$l/l carbon dioxide, and in the presence or absence of 3% sucrose.
Figure 10:
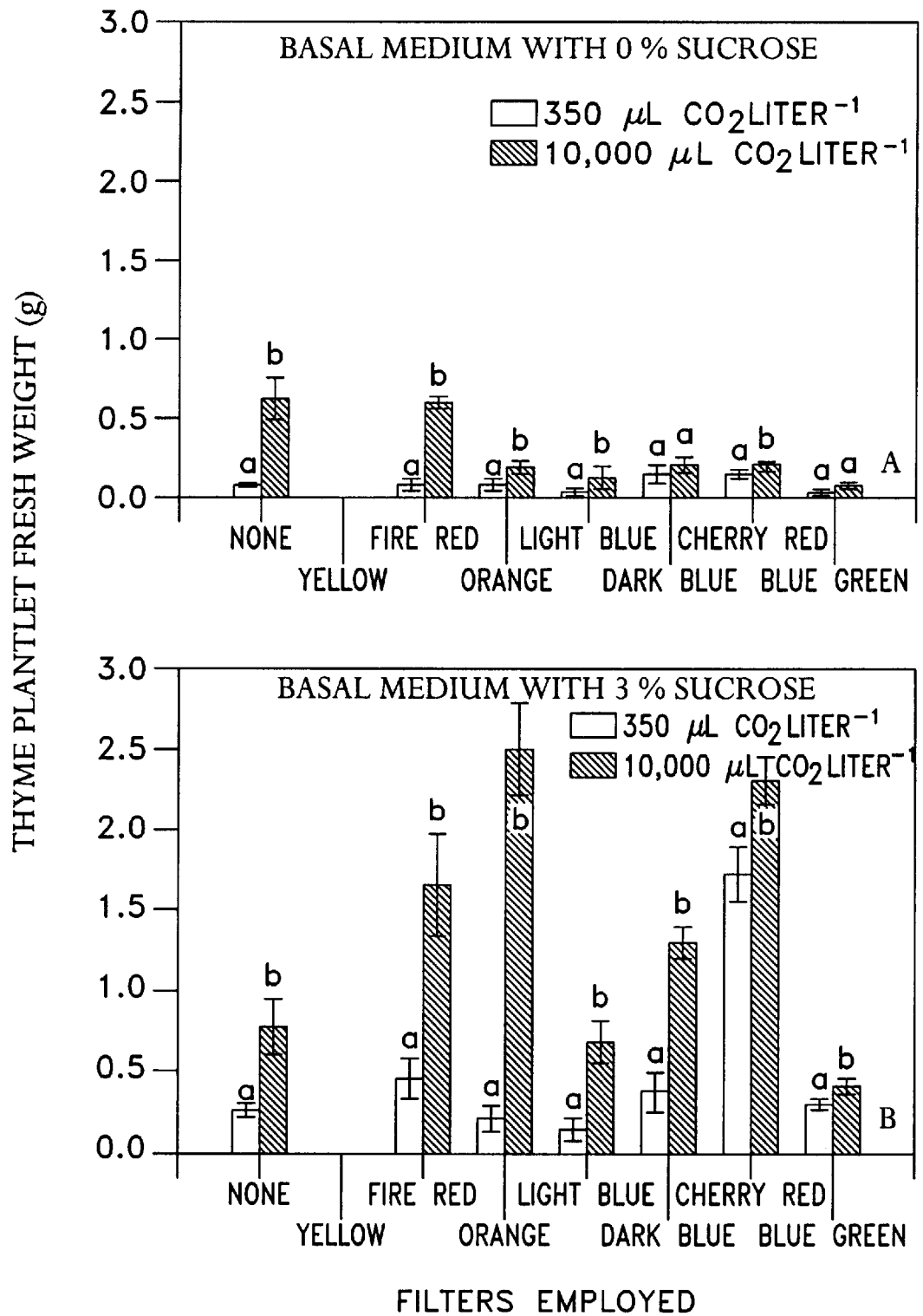
FIGS. 10A–10B display bar graphs that illustrate the effect on thyme plantlet fresh weight of light color, with and without exposure to 10,000 $\mu$l/l carbon dioxide, and in the presence or absence of 3% sucrose.
Figure 11:
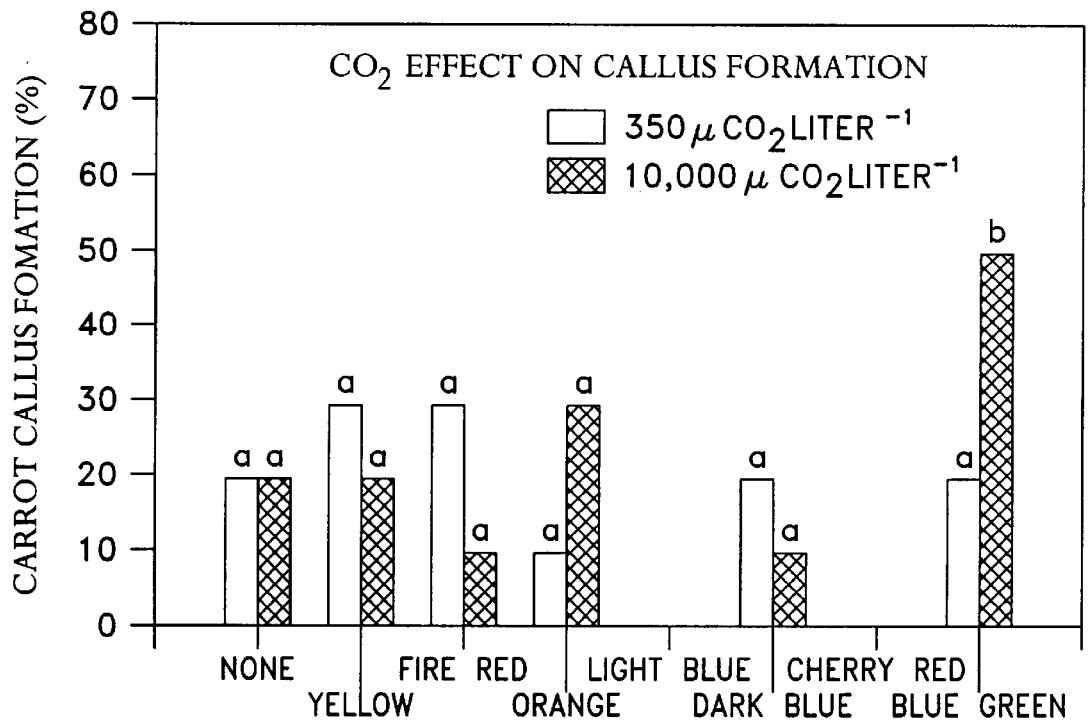
FIG. 11 displays a bar graph that illustrates that effect on carrot callus formation of light color with and without exposure to 10,000 $\mu$l/l carbon dioxide.

The results are presented in FIG. 8, which is two bar graphs displaying the fresh weights and shoots/culture as a function of the procedure used to grow the cultures. Best growth responses were obtained using 15 minute soakings 4 times daily within the bioreactor coupled to periodic $CO_2$ aeration treatments. Worst growth, in terms of fresh weight and shoot number, was obtained in continuous liquid medium (second column on graphs of FIG. 8). Experiments were repeated at least 2 times and a representative replication is presented. Media was replaced every 4 weeks. Mean separation by Student-Newman-Keuls multiple range test. Columns with the same letter on top were not significantly different.

Within the continuous liquid system, cultures quickly browned and died and did not exhibit any desirable growth responses at all. If we compare growth obtained with the agar medium (first column in FIG. 8 graphs) as our control standard cultures, cultures grown in the bioreactor can be seen to be superior regardless of the number of soakings administered (FIG. 8). Increasing the number of soakings from once daily to 4 times daily doubles the fresh weight and number of shoots produced per culture. Fresh weights and number of shoots/culture increased 10.9-fold when cultures were grown in the bioreactor and soaked 4 times daily compared to culture chamber atmosphere using charcoal filtered air (i.e. 350) or 10,000 $\mu$l/l liter$^{-1}$ $CO_2$ enhanced sweetgum culture growth. For example, culture fresh weight increased 11.9-fold and 16.3-fold, respectively, using the bioreactor with periodic air and $CO_2$ flushing, compared to growth obtained from sweetgum grown on agar medium.

EXAMPLE 8

FIGS. 9–12 present data from experiments designed to illustrate the influence of various light filters with or without the benefit of supplemental enrichment with 10,000 $\mu$l/l liter$^{-1}$ $CO_2$. The light filters used were yellow, fire red, orange, light blue, dark blue, cherry red and blue green, and were purchased from ROSCO Corporation, Port Chester, N.Y. The plant cultures were prepared and grown in accordance with Example 1.

Lettuce and thyme tissue cultures fresh weights increased dramatically when filters were supplemented with 10,000 $\mu$l/l liter$^{-1}$ $CO_2$ whether 3% sucrose was included in the medium or not. Various filters have different effects on growth depending on the species tested and supplementation with $CO_2$. For example, with lettuce grown on basal medium (i.e., minimal MS salts recited above) with 3% sucrose, the fire red filter allowed for only modest growth when compared to control (i.e. no filter) but when supplemented with 10,000 $\mu$l/l liter$^{-1}$ $CO_2$ maximum fresh weights were obtained that compared favorably to all other treatments. Also, carrot grown under the blue-green filter expressed enhanced callusing when enhanced $CO_2$ was administered.

Figure 12:
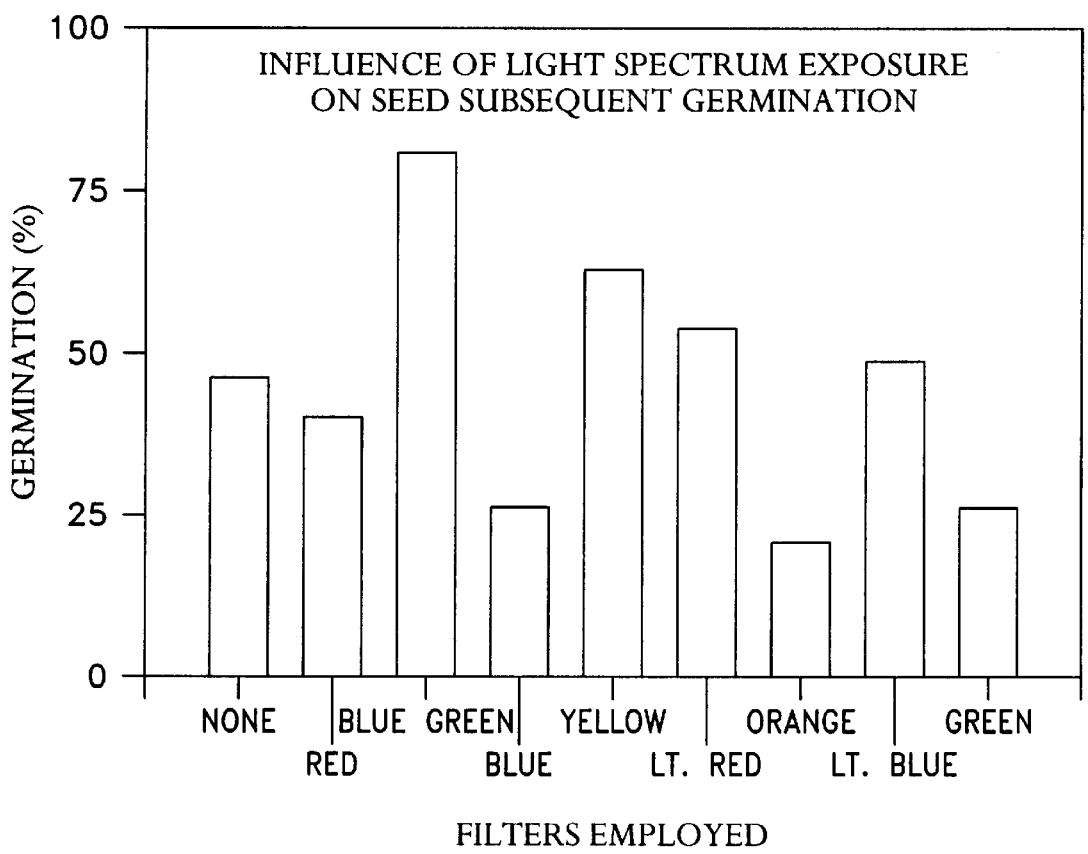
FIG. 12 displays a bar graph that illustrates the influence of light spectrum exposure on seed germination in loblolly pine.

Filters were also found to influence pine seed germination as shown in FIG. 12. Loblolly pine seeds were found to exhibit enhanced germination on blue-green filters compared to control treatments. It is of interest to note that while pine vegetation growth was promoted by red light, germination was promoted by blue-green light. Germination and vegetative growth are different physiological processes and accordingly respond differently to the stimulus provided by light coupled with $CO_2$. This result, as well as the observation that lettuce and thyme each have a preferred wavelength/$CO_2$ combination for maximum growth, illustrates that for each species (and physiological process under investigation) a variety of wavelengths must be tested empirically to find the optimum. Such testing is easily performed by one skilled in the art with readily available filters.

EXAMPLE 9

This example illustrates the response of sweetgum microshoots on soilless medium.

Sweetgum shoot cultures were prepared by the method of Sutter & Barker in accordance with Example 1 and grown in the bioreactor of the present invention. Sweetgum microshoots were harvested at about 1 and 2 cm in length, dipped in a commercial rooting powder (0.37% IBA) and set in a soilless medium of equal parts peat:vermiculite and perlite. $CO_2$ concentrations of 350, 1,500, 3,000, 10,000, and 30,000 $\mu$l liter$^{-1}$ $CO_2$ were provided by means of the apparatus shown in FIG. 2. The results are present in Table 2. Rooting and survival were optimized at a $CO_2$ concentration of 10,000 $\mu$l/l.

TABLE 2

Influence of Various levels of Carbon Dioxide levels on Percent "Rooting and Survival of Sweetgum Shoots ex vitro. Shoots were grown in soil for 4 weeks before data was taken.*

| $CO_2$ Concentrations ($\mu$L liter$^{-1}$ $CO_2$) | Shoot length (cm) | |
|---|---|---|
| | 1 | 2 |
| 350 | 50 a | 63 a |
| 1,500 | 50 a | 63 a |
| 3,000 | 63 a | 69 a |
| 10,000 | 92 b | 94 b |
| 30,000 | 63 a | 63 a |

*Treatments sharing the same letter in the same column are not significantly different using the Fisher's Exact test ($P < 0.5$).

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow:

What is claimed:

1. A method of propagating woody plant material comprising exposing the plant material to a pulse of substantially only red light and culturing the plant material in a concentration of carbon dioxide in excess of 1000 $\mu$l/l.

2. The method of claim 1, wherein the step of exposing the plant material occurs in vitro.

3. The method of claim 1, wherein the step of exposing the plant material occurs in non-aseptic conditions.

4. The method of claim 1, wherein the plant material comprises tissue culture, seedlings, cuttings or microshoots from tissue culture.

5. The method of claim 1, wherein the woody plant material is from sweetgum, sycamore, oak, green ash, Douglas fir, Populus spp., Eucalyptus spp., Pinus spp., Acacia spp., Picea spp., Larix spp., Abies spp., or Gmelina trees.

6. The method of claim 1, wherein the concentration of carbon dioxide ranges from more than 1000 $\mu$l/l to about 50,000 $\mu$l/l.

7. The method of claim 6, wherein the concentration of carbon dioxide ranges from about 7500 $\mu$l/l to about 30,000 $\mu$l/l.

8. The method of claim 1, further comprising:
(a) introducing the plant material into a chamber;
(b) introducing a nutrient medium into the chamber; and
(c) removing the nutrient medium from the chamber.

9. A method for propagating woody plant material comprising culturing the plant material in excess of a concentration of carbon dioxide of 7000 $\mu$l/l.

10. The method of claim 9, further comprising exposing the plant material to a pulse of substantially only red light.

11. The method of claim 9, wherein the concentration of carbon dioxide is at from about 7000 $\mu$l/l to about 50,000 $\mu$l/l.

12. The method of claim 9, further comprising:
(a) introducing the plant material into a chamber;
(b) exposing the plant material to a pulse of substantially only red light;
(c) introducing a nutrient medium into the chamber; and
(d) removing the nutrient medium from the chamber.

13. The method of claim 12, further comprising: (e) monitoring the pH value of the medium; and (f) adjusting the pH value of the medium to maintain a pH value of between about 4 and about 6.

14. The method of claim 12, further comprising the step of exposing the plant material to about sixteen continuous hours of unfiltered light out of every twenty-four hours.

\* \* \* \* \*